(12) United States Patent
Fink et al.

(10) Patent No.: US 7,332,282 B2
(45) Date of Patent: Feb. 19, 2008

(54) COMPOSITIONS AND METHODS FOR DETECTING AND TREATING NEUROLOGICAL CONDITIONS

(75) Inventors: John K. Fink, Ann Arbor, MI (US); Shirley Rainier, Sylvania, OH (US); Robert D. Nicholls, Philadelphia, PA (US); Jinghua Chai, Ardmore, PA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 248 days.

(21) Appl. No.: 10/921,742

(22) Filed: Aug. 19, 2004

(65) Prior Publication Data

US 2005/0164228 A1    Jul. 28, 2005

Related U.S. Application Data

(60) Provisional application No. 60/496,317, filed on Aug. 19, 2003.

(51) Int. Cl.
*C07H 21/04* (2006.01)
*C12Q 1/68* (2006.01)

(52) U.S. Cl. .................. 435/6; 435/91.1; 435/91.2; 536/23.1; 536/24.3

(58) Field of Classification Search ................ None
See application file for complete search history.

(56) References Cited

U.S. PATENT DOCUMENTS

2003/0092019 A1*  5/2003  Meyer et al. ............ 435/6

FOREIGN PATENT DOCUMENTS

CN    1618814    *  5/2005

OTHER PUBLICATIONS

Rainer et al. (Am. J. Hum. Genetics, vol. 73, pp. 967-971, 2003).*
Kaneko et al. (Movement Disorders, vol. 21, No. 9, 2006).*
Chen et al. (Human Mutations, vol. 25, pp. 135-141, 2005).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Fink et al., "The hereditary spastic paraplegias," Arch Neurol. 60:1045-1045 (2003).
Rainier et al., "NIPA1 gene mutations cause autosomal dominant hereditary spastic paraplegia (SPG6)," Am J Hum Genet 73:967-971 (2003).
Reed et al., "A novel NIPA1 mutation associated with a pure form of autosomal dominant hereditary spastic paraplegia," Neurogenetics 6:79-84 (2005).
Chen et al., "Distinct novel mutations affecting the same base in NAIPA1 gene cause autosomal dominant hereditary spastic paraplegia in two chinese families," Hum Mutation 25:135-141 (2005).

* cited by examiner

*Primary Examiner*—Jeanine A. Goldberg
(74) *Attorney, Agent, or Firm*—Casimir Jones, S.C.

(57) ABSTRACT

The present invention relates to the NIPA-1 proteins and nucleic acids encoding the NIPA-1 proteins. The present invention further provides assays for the detection of NIPA-1 polymorphisms and mutations associated with disease states, as well as methods of screening for ligands and modulators of NIPA-1 proteins.

8 Claims, 13 Drawing Sheets

SPG6 occurs in regions deleted in Prader-Willi (PWS) and Angleman syndromes (AS)

NIPA1 predicted secondary structure

Figure 6 – SEQ ID NO: 1

| | |
|---|---|
| 1 | ATGGGGACTGCAGCTGCGGCAGCGGCGGCGGCGGCGGCGGCGGCCGGGGAGGGGGCGCGTAGCCCGAGCCCCGCCGC |
| 81 | CGTGTCGCTCGGCCTGGGCGTGGCCGTCGTGTCGAGCCTGGTGAACGGGTCCACGTTCGTGCTACAGAAGAAGGGCATCG |
| 161 | TGCGTGCCAAGCGGCGAGGTACTTCCTATTTAACAGACATTGTGTGGTGGGCTGGCACAATCGCAATGGCTGTTGGCCAG |
| 241 | ATTGGAAACTTCCTGGCTTACACGGCGGTCCCCACGGTCCTGGTAACCCCCCTGGGCGCCCTTGGAGTACCGTTCGGGTC |
| 321 | CATTTTAGCTTCCTATCTCCTGAAGGAAAAGCTCAACATCTTGGGCAAGTTGGGGTGCCTGCTAAGCTGTGCAGGCTCCG |
| 401 | TCGTGCTGATTATCCACTCCCCAAAGTCTGAGAGTGTGACGACTCAGGCTGAGCTGGAGGAAAAGCTGACCAACCCAGTG |
| 481 | TTTGTGGGCTACCTGTGCATCGTGCTGCTCATGCTGCTGCTGCTCATCTTCTGGATCGCGCCGGCCCATGGGCCCACCAA |
| 561 | CATCATGGTCTACATCAGCATCTGCTCCTTGCTGGGCAGTTTCACCGTGCCTTCCACCAAGGGCATCGGGCTGGCGGCCC |
| 641 | AAGACATCTTGCATAACAACCCGTCCAGTCAGAGAGCCCTCTGCCTGTGCCTGGTACTCCTGGCCGTGCTCGGCTGCAGC |
| 721 | ATCATCGTCCAGTTCAGGTACATCAACAAGGCGCTGGAGTGCTTCGACTCCTCGGTGTTCGGGGCCATCTACTACGTCGT |
| 801 | GTTTACCACGCTGGTCCTGCTGGCCTCAGCCATCCTCTTCCGGGAGTGGAGCAACGTGGGCCTGGTGGACTTCTTGGGGA |
| 881 | TGGCCTGTGGATTCACGACCGTCTCCGTGGGGATTGTCCTTATACAGGTGTTCAAAGAGTTCAATTTCAACCTTGGGGAG |
| 961 | ATGAACAAATCTAATATGAAAACAGACTAGATTGCAATAGGAGCTTGGATGGTTCGAGGAATAGGCATTGGAGGTGGTTT |
| 1041 | CTGGCCGTGATTGGATGTGAAGTAGAAGAGGTCCTCGATCATGGTGTTAGAATTGACTGGATAGTAACAGGTGGTCTGGT |
| 1121 | GGATAGCGGGGAGCATGGCTCAGCACCAGAGCAGAGGCCCAGCCAGCCCTCTGCAGCCCAAACGTCCCCAACGGTTGCCT |
| 1201 | GGCACCATCTCTCTCTGATGAGACGAATCTCATTTTCATTTCCATTAACCTGGAAGCTTTCATGAATATTCTCTTCTTTT |
| 1281 | AAAACATTTTAACATTATTTAAACAGAAAAAGATGGGCTCTTTCTGGTTAGTTGTTACATGATAGCAGAGATATTTTTAC |
| 1361 | TTAGATTACTTTGGGAATGAGAGATTGTTGTCTTGAACTCTGGCACTGTACAGTGAATGTGTCTGTAGTTGTGTTAGTTT |
| 1441 | GCATTAAGCATGTATAACATTCAAGTATGTCATCCAAATAAGAGGCATATACATTGAATTGTTTTTAATCCTCTGACAAG |
| 1521 | TTGACTCTTCGACCCCCACCCCCACCCAAGACATTTTAATAGTAAATAGAGAGAGAGAAGAGTTAATGAACATGAGGT |
| 1601 | AGTGTTCCACTGGCAGGATGACTTTTCAATAGCTCAAATCAATTTCAGTGCCTTTATCACTTGAATTATTAACTTAATTT |
| 1681 | GACTCTTAATGTGTATATGTTCTTAGATTAGAATAATGCAACTTCGAGTATGCTTTAATATTTCAATATTCAAGTTACAA |
| 1761 | ATGTATAAGGCAGTTAGAAATAATACAGTCACATGTCACTTAATGATAGGGAAACATTCTGAGAAATGCATTGTAAGGTG |
| 1841 | ACTTTATTGTGTGAACATCATGGAGTGCACTTATACAAACCTAGATGGGACACCTATGACCCACCCAGGCCAGATGGTAC |
| 1921 | AGCCTGTTGCTCCTGGGCCACACACCTGTACAGCATGTGACCGCACTGAATACCGCAGGCAATTGTAACACAGTGGTGAG |
| 2001 | TATTTGTGTTTACAAACATAGGAAAGGTACAGTAAAACTATGGTATTACAATGTTATGGGACCACCGTCATGTAAGTGGT |
| 2081 | ATGTCTTTGACAGAAACATGGTTACGTGGTTCATGACTGTATATTCACTGGAAGATAGTCAAGACTAAAGACACATTAGA |
| 2161 | GCAAATTGACCCCTTTAACATGTGATTATTGTCCAATTAAAGACAGTTGATTTAAGTAGCAT |

Figure 7 – SEQ ID NO: 2

| | |
|---|---|
| 1 | ATGGGGACTGCAGCTGCGGCAGCGGCGGCGGCGGCGGCGGCCGGGGAGGGGGCGCGTAGCCCGAGCCCCGCCGC |
| 81 | CGTGTCGCTCGGCCTGGGCGTGGCCGTCGTGTCGAGCCTGGTGAACGGGTCCAGGTTCGTGCTACAGAAGAAGGGCATCG |
| 161 | TGCGTGCCAAGCGGCGAGGTACTTCCTATTTAACAGACATTGTGTGGTGGGCTGGCACAATCGCAATGGCTGTTGGCCAG |
| 241 | ATTGGAAACTTCCTGGCTTACACGGCGGTCCCCACGGTCCTGGTAACCCCCCTGGGCGCCCTTGGAGTACCGTTCGGGTC |
| 321 | CATTTTAGCTTCCTATCTCCTGAAGGAAAAGCTCAACATCTTGGGCAAGTTGGGGTGCCTGCTAAGCTGTGCAGGCTCCG |
| 401 | TCGTGCTGATTATCCACTCCCCAAAGTCTGAGAGTGTGACGACTCAGGCTGAGCTGGAGGAAAAGCTGACCAACCCAGTG |
| 481 | TTTGTGGGCTACCTGTGCATCGTGCTGCTCATGCTGCTGCTGCTCATCTTCTGGATCGCGCCGGCCCATGGGCCCACCAA |
| 561 | CATCATGGTCTACATCAGCATCTGCTCCTTGCTGGGCAGTTTCACCGTGCCTTCCACCAAGGGCATCGGGCTGGCGGCCC |
| 641 | AAGACATCTTGCATAACAACCCGTCCAGTCAGAGAGCCCTCTGCCTGTGCCTGGTACTCCTGGCCGTGCTCGGCTGCAGC |
| 721 | ATCATCGTCCAGTTCAGGTACATCAACAAGGCGCTGGAGTGCTTCGACTCCTCGGTGTTCGGGGCCATCTACTACGTCGT |
| 801 | GTTTACCACGCTGGTCCTGCTGGCCTCAGCCATCCTCTTCCGGGAGTGGAGCAACGTGGGCCTGGTGGACTTCTTGGGGA |
| 881 | TGGCCTGTGGATTCACGACCGTCTCCGTGGGGATTGTCCTTATACAGGTGTTCAAAGAGTTCAATTTCAACCTTGGGGAG |
| 961 | ATGAACAAATCTAATATGAAAACAGACTAGATTGCAATAGGAGCTTGGATGGTTCGAGGAATAGGCATTGGAGGTGGTTT |
| 1041 | CTGGCCGTGATTGGATGTGAAGTAGAAGAGGTCCTCGATCATGGTGTTAGAATTGACTGGATAGTAACAGGTGGTCTGGT |
| 1121 | GGATAGCGGGGAGCATGGCTCAGCACCAGAGCAGAGGCCCAGCCAGCCCTCTGCAGCCCAAACGTCCCCAACGGTTGCCT |
| 1201 | GGCACCATCTCTCTCTGATGAGACGAATCTCATTTTCATTTCCATTAACCTGGAAGCTTTCATGAATATTCTCTTCTTTT |
| 1281 | AAAACATTTTAACATTATTTAAACAGAAAAAGATGGGCTCTTTCTGGTTAGTTGTTACATGATAGCAGAGATATTTTTAC |
| 1361 | TTAGATTACTTTGGGAATGAGAGATTGTTGTCTTGAACTCTGGCACTGTACAGTGAATGTGTCTGTAGTTGTGTTAGTTT |
| 1441 | GCATTAAGCATGTATAACATTCAAGTATGTCATCCAAATAAGAGGCATATACATTGAATTGTTTTTAATCCTCTGACAAG |
| 1521 | TTGACTCTTCGACCCCCACCCCCACCCAAGACATTTTAATAGTAAATAGAGAGAGAGAGAAGAGTTAATGAACATGAGGT |
| 1601 | AGTGTTCCACTGGCAGGATGACTTTTCAATAGCTCAAATCAATTTCAGTGCCTTTATCACTTGAATTATTAACTTAATTT |
| 1681 | GACTCTTAATGTGTATATGTTCTTAGATTAGAATAATGCAACTTCGAGTATGCTTTAATATTTCAATATTCAAGTTACAA |
| 1761 | ATGTATAAGGCAGTTAGAAATAATACAGTCACATGTCACTTAATGATAGGGAAACATTCTGAGAAATGCATTGTAAGGTG |
| 1841 | ACTTTATTGTGTGAACATCATGGAGTGCACTTATACAAACCTAGATGGGACACCTATGACCCACCCAGGCCAGATGGTAC |
| 1921 | AGCCTGTTGCTCCTGGGCCACACACCTGTACAGCATGTGACCGCACTGAATACCGCAGGCAATTGTAACACAGTGGTGAG |
| 2001 | TATTTGTGTTTACAAACATAGGAAAGGTACAGTAAAACTATGGTATTACAATGTTATGGGACCACCGTCATGTAAGTGGT |
| 2081 | ATGTCTTTGACAGAAACATGGTTACGTGGTTCATGACTGTATATTCACTGGAAGATAGTCAAGACTAAAGACACATTAGA |
| 2161 | GCAAATTGACCCCTTTAACATGTGATTATTGTCCAATTAAAGACAGTTGATTTAAGTAGCAT |

Figure 8 – SEQ ID NO: 3

```
              10         20         30         40         50
  0   MGTAAAAAAA AAAAAAGEGA RSPSPAAVSL GLGVAVVSSL VNGSTFVLQK
 50   KGIVRAKRRG TSYLTDIVWW AGTIAMAVGQ IGNFLAYTAV PTVLVTPLGA
100   LGVPFGSILA SYLLKEKLNI LGKLGCLLSC AGSVVLIIHS PKSESVTTQA
150   ELEEKLTNPV FVGYLCIVLL MLLLLIFWIA PAHGPTNIMV YISICSLLGS
200   FTVPSTKGIG LAAQDILHNN PSSQRALCLC LVLLAVLGCS IIVQFRYINK
250   ALECFDSSVF GAIYYVVFTT LVLLASAILF REWSNVGLVD FLGMACGFTT
300   VSVGIVLIQV FKEFNFNLGE MNKSNMKTD
```

Figure 9 – SEQ ID NO: 4

```
             10          20          30          40          50
  0   MGTAAAAAAA  AAAAAAGEGA  RSPSPAAVSL  GLGVAVVSSL  VNGSRFVLQK
 50   KGIVRAKRRG  TSYLTDIVWW  AGTIAMAVGQ  IGNFLAYTAV  PTVLVTPLGA
100   LGVPFGSILA  SYLLKEKLNI  LGKLGCLLSC  AGSVVLIIHS  PKSESVTTQA
150   ELEEKLTNPV  FVGYLCIVLL  MLLLLIFWIA  PAHGPTNIMV  YISICSLLGS
200   FTVPSTKGIG  LAAQDILHNN  PSSQRALCLC  LVLLAVLGCS  IIVQFRYINK
250   ALECFDSSVF  GAIYYVVFTT  LVLLASAILF  REWSNVGLVD  FLGMACGFTT
300   VSVGIVLIQV  FKEFNFNLGE  MNKSNMKTD
```

Figure 10 – SEQ ID NO: 5

| 1 | GGCTCGGAGGGCGGGCGCGGGCGGAATGGGGACTGCAGCTGCGGCAGCGGCGGCGGCGGCGGCGGCGGCCGGGGAGG |
|---|---|
| 81 | GGGCGCGTAGCCCGAGCCCCGCCGCCGTGTCGCTCGGCCTGGGCGTGGCCGTCGTGTCGAGCCTGGTGAACGGGTCCACG |
| 161 | TTCGTGCTACAGAAGAAGGGCATCGTGCGTGCCAAGCGGCGAGGTACTTCCTATTTAACAGACATTGTGTGGTGGGCTGG |
| 241 | CACAATCGCAATGGCTGTTGGCCAGATTGGAAACTTCCTGGCTTACACGGCGGTCCCCACGGTCCTGGTAACCCCCCTGG |
| 321 | GCGCCCTTGGAGTACCGTTCGGGTCCATTTTAGCTTCCTATCTCCTGAAGGAAAAGCTCAACATCTTGGGCAAGTTGGGG |
| 401 | TGCCTGCTAAGCTGTGCAGGCTCCGTCGTGCTGATTATCCACTCCCCAAAGTCTGAGAGTGTGACGACTCAGGCTGAGCT |
| 481 | GGAGGAAAAGCTGACCAACCCAGTGTTTGTGGGCTACCTGTGCATCGTGCTGCTCATGCTGCTGCTGCTCATCTTCTGGA |
| 561 | TCGCGCCGGCCCATGGGCCCACCAACATCATGGTCTACATCAGCATCTGCTCCTTGCTGGGCAGTTTCACCGTGCCTTCC |
| 641 | ACCAAGGGCATCGGGCTGCGGCCCAAGACATCTTGCATAACAACCCGTCCAGTCAGAGAGCCCTCTGCCTGTGCCTGGT |
| 721 | ACTCCTGGCCGTGCTCGGCTGCAGCATCATCGTCCAGTTCAGGTACATCAACAAGGCGCTGGAGTGCTTCGACTCCTCGG |
| 801 | TGTTCGGGGCCATCTACTACGTCGTGTTTACCACGCTGGTCCTGCTGGCCTCAGCCATCCTCTTCCGGGAGTGGAGCAAC |
| 881 | GTGGGCCTGGTGGACTTCTTGGGGATGGCCTGTGGATTCACGACCGTCTCCGTGGGGATTGTCCTTATACAGGTGTTCAA |
| 961 | AGAGTTCAATTTCAACCTTGGGGAGATGAACAAATCTAATATGAAAACAGACTAGATTGCAATAGGAGCTTGGATGGTTC |
| 1041 | GAGGAATAGGCATTGGAGGTGGTTTCTGGCCGTGATTGGATGTGAAGTAGAAGAGGTCCTCGATCATGGTGTTAGAATTG |
| 1121 | ACTGGATAGTAACAGGTGGTCTGGTGGATAGCGGGGAGCATGGCTCAGCACCAGAGCAGAGGCCCAGCCAGCCCTCTGCA |
| 1201 | GCCCAAACGTCCCCAACGGTTGCCTGGCACCATCTCTCTCTGATGAGACGAATCTCATTTTCATTTCCATTAACCTGGAA |
| 1281 | GCTTTCATGAATATTCTCTTCTTTTAAAACATTTTAACATTATTTAAACAGAAAAAGATGGGCTCTTTCTGGTTAGTTGT |
| 1361 | TACATGATAGCAGAGATATTTTTACTTAGATTACTTTGGGAATGAGAGATTGTTGTCTTGAACTCTGGCACTGTACAGTG |
| 1441 | AATGTGTCTGTAGTTGTGTTAGTTTGCATTAAGCATGTATAACATTCAAGTATGTCATCCAAATAAGAGGCATATACATT |
| 1521 | GAATTGTTTTTAATCCTCTGACAAGTTGACTCTTCGACCCCCACCCCCACCCAAGACATTTTAATAGTAAATAGAGAGAG |
| 1601 | AGAGAAGAGTTAATGAACATGAGGTAGTGTTCCACTGGCAGGATGACTTTTCAATAGCTCAAATCAATTTCAGTGCCTTT |
| 1681 | ATCACTTGAATTATTAACTTAATTTGACTCTTAATGTGTATATGTTCTTAGATTAGAATAATGCAACTTCGAGTATGCTT |
| 1761 | TAATATTTCAATATTCAAGTTACAAATGTATAAGGCAGTTAGAAATAATACAGTCACATGTCACTTAATGATAGGGAAAC |
| 1841 | ATTCTGAGAAATGCATTGTAAGGTGACTTTATTGTGTGAACATCATGGAGTGCACTTATACAAACCTAGATGGGACACCT |
| 1921 | ATGACCCACCCAGGCCAGATGGTACAGCCTGTTGCTCCTGGGCCACACACCTGTACAGCATGTGACCGCACTGAATACCG |
| 2001 | CAGGCAATTGTAACACAGTGGTGAGTATTTGTGTTTACAAACATAGGAAAGGTACAGTAAAACTATGGTATTACAATGTT |
| 2081 | ATGGGACCACCGTCATGTAAGTGGTATGTCTTTGACAGAAACATGGTTACGTGGTTCATGACTGTATATTCACTGGAAGA |
| 2161 | TAGTCAAGACTAAAGACACATTAGAGCAAATTGACCCCTTTAACATGTGATTATTGTCCAATTAAAGACAGTTGATTTAA |
| 2241 | GTAGCAT |

Figure 11 – SEQ ID NO: 6

| | |
|---|---|
| 1 | GGCTCGGAGGGCGGGCGCGGGCGGAATGGGGACTGCAGCTGCGGCAGCGGCGGCGGCGGCGGCGGCGGCCGGGGAGG |
| 81 | GGGCGCGTAGCCCGAGCCCCGCCGCCGTGTCGCTCGGCCTGGGCGTGGCCGTCGTGTCGAGCCTGGTGAACGGGTCCAGg |
| 161 | TTCGTGCTACAGAAGAAGGGCATCGTGCGTGCCAAGCGGCGAGGTACTTCCTATTTAACAGACATTGTGTGGTGGGCTGG |
| 241 | CACAATCGCAATGGCTGTTGGCCAGATTGGAAACTTCCTGGCTTACACGGCGGTCCCCACGGTCCTGGTAACCCCCCTGG |
| 321 | GCGCCCTTGGAGTACCGTTCGGGTCCATTTTAGCTTCCTATCTCCTGAAGGAAAAGCTCAACATCTTGGGCAAGTTGGGG |
| 401 | TGCCTGCTAAGCTGTGCAGGCTCCGTCGTGCTGATTATCCACTCCCCAAAGTCTGAGAGTGTGACGACTCAGGCTGAGCT |
| 481 | GGAGGAAAAGCTGACCAACCCAGTGTTTGTGGGCTACCTGTGCATCGTGCTGCTCATGCTGCTGCTGCTCATCTTCTGGA |
| 561 | TCGCGCCGGCCCATGGGCCCACCAACATCATGGTCTACATCAGCATCTGCTCCTTGCTGGGCAGTTTCACCGTGCCTTCC |
| 641 | ACCAAGGGCATCGGGCTGGCGGCCCAAGACATCTTGCATAACAACCCGTCCAGTCAGAGAGCCCTCTGCCTGTGCCTGGT |
| 721 | ACTCCTGGCCGTGCTCGGCTGCAGCATCATCGTCCAGTTCAGGTACATCAACAAGGCGCTGGAGTGCTTCGACTCCTCGG |
| 801 | TGTTCGGGGCCATCTACTACGTCGTGTTTACCACGCTGGTCCTGCTGGCCTCAGCCATCCTCTTCCGGGAGTGGAGCAAC |
| 881 | GTGGGCCTGGTGGACTTCTTGGGGATGGCCTGTGGATTCACGACCGTCTCCGTGGGGATTGTCCTTATACAGGTGTTCAA |
| 961 | AGAGTTCAATTTCAACCTTGGGGAGATGAACAAATCTAATATGAAAACAGACTAGATTGCAATAGGAGCTTGGATGGTTC |
| 1041 | GAGGAATAGGCATTGGAGGTGGTTTCTGGCCGTGATTGGATGTGAAGTAGAAGAGGTCCTCGATCATGGTGTTAGAATTG |
| 1121 | ACTGGATAGTAACAGGTGGTCTGGTGGATAGCGGGGAGCATGGCTCAGCACCAGAGCAGAGGCCCAGCCAGCCCTCTGCA |
| 1201 | GCCCAAACGTCCCCAACGGTTGCCTGGCACCATCTCTCTGATGAGACGAATCTCATTTTCATTTCCATTAACCTGGAA |
| 1281 | GCTTTCATGAATATTCTCTTCTTTTAAAACATTTTAACATTATTTAAACAGAAAAAGATGGGCTCTTTCTGGTTAGTTGT |
| 1361 | TACATGATAGCAGAGATATTTTACTTAGATTACTTTGGGAATGAGAGATTGTTGTCTTGAACTCTGGCACTGTACAGTG |
| 1441 | AATGTGTCTGTAGTTGTGTTAGTTTGCATTAAGCATGTATAACATTCAAGTATGTCATCCAAATAAGAGGCATATACATT |
| 1521 | GAATTGTTTTTAATCCTCTGACAAGTTGACTCTTCGACCCCCACCCCCACCCAAGACATTTTAATAGTAAATAGAGAGAG |
| 1601 | AGAGAAGAGTTAATGAACATGAGGTAGTGTTCCACTGGCAGGATGACTTTTCAATAGCTCAAATCAATTTCAGTGCCTTT |
| 1681 | ATCACTTGAATTATTAACTTAATTTGACTCTTAATGTGTATATGTTCTTAGATTAGAATAATGCAACTTCGAGTATGCTT |
| 1761 | TAATATTTCAATATTCAAGTTACAAATGTATAAGGCAGTTAGAAATAATACAGTCACATGTCACTTAATGATAGGGAAAC |
| 1841 | ATTCTGAGAAATGCATTGTAAGGTGACTTTATTGTGTGAACATCATGGAGTGCACTTATACAAACCTAGATGGGACACCT |
| 1921 | ATGACCCACCCAGGCCAGATGGTACAGCCTGTTGCTCCTGGGCCACACACCTGTACAGCATGTGACCGCACTGAATACCG |
| 2001 | CAGGCAATTGTAACACAGTGGTGAGTATTTGTGTTTACAAACATAGGAAAGGTACAGTAAAACTATGGTATTACAATGTT |
| 2081 | ATGGGACCACCGTCATGTAAGTGGTATGTCTTTGACAGAAACATGGTTACGTGGTTCATGACTGTATATTCACTGGAAGA |
| 2161 | TAGTCAAGACTAAAGACACATTAGAGCAAATTGACCCCTTTAACATGTGATTATTGTCCAATTAAAGACAGTTGATTTAA |
| 2241 | GTAGCAT |

Figure 12 – SEQ ID NO: 7

```
             10         20         30         40         50
  0   ARRAGAGGMG TAAAAAAAAA AAAAGEGARS PSPAAVSLGL GVAVVSSLVN
 50   GSTFVLQKKG IVRAKRRGTS YLTDIVWWAG TIAMAVGQIG NFLAYTAVPT
100   VLVTPLGALG VPFGSILASY LLKEKLNILG KLGCLLSCAG SVVLIIHSPK
150   SESVTTQAEL EEKLTNPVFV GYLCIVLLML LLLIFWIAPA HGPTNIMVYI
200   SICSLLGSFT VPSTKGIGLA AQDILHNNPS SQRALCLCLV LLAVLGCSII
250   VQFRYINKAL ECFDSSVFGA IYYVVFTTLV LLASAILFRE WSNVGLVDFL
300   GMACGFTTVS VGIVLIQVFK EFNFNLGEMN KSNMKTD!IA IGAWMVRGIG
350   IGGGFWP!LD VK!KRSSIMV LELTG!!QVV WWIAGSMAQH QSRGPASPLQ
400   PKRPQRLPGT ISL!!DESHF HFH!PGSFHE YSLLLKHFNI I!TEKDGLFL
450   VSCYMIAEIF LLRLLWE!EI VVLNSGTVQ! MCL!LC!FAL SMYNIQVCHP
500   NKRHIH!IVF NPLTS!LFDP HPHPRHFNSK !REREELMNM R!CSTGRMTF
550   Q!LKSISVPL SLELLT!FDS !CVYVLRLE! CNFEYALIFQ YSSYKCIRQL
600   EIIQSHVT!! !GNILRNAL! GDFIV!TSWS ALIQT!MGHL !PTQARWYSL
650   LLLGHTPVQH VTALNTAGNC NTVVSICVYK HRKGTVKLWY YNVMGPPSCK
700   WYVFDRNMVT WFMTVYSLED SQD!RHIRAN !PL!HVIIVQ LKTVDLSS
```

Figure 13 – SEQ ID NO: 8

|     | 10 | 20 | 30 | 40 | 50 |
|-----|----|----|----|----|----|
| 0   | ARRAGAGGMG | TAAAAAAAAA | AAAAGEGARS | PSPAAVSLGL | GVAVVSSLVN |
| 50  | GSRFVLQKKG | IVRAKRRGTS | YLTDIVWWAG | TIAMAVGQIG | NFLAYTAVPT |
| 100 | VLVTPLGALG | VPFGSILASY | LLKEKLNILG | KLGCLLSCAG | SVVLIIHSPK |
| 150 | SESVTTQAEL | EEKLTNPVFV | GYLCIVLLML | LLLIFWIAPA | HGPTNIMVYI |
| 200 | SICSLLGSFT | VPSTKGIGLA | AQDILHNNPS | SQRALCLCLV | LLAVLGCSII |
| 250 | VQFRYINKAL | ECFDSSVFGA | IYYVVFTTLV | LLASAILFRE | WSNVGLVDFL |
| 300 | GMACGFTTVS | VGIVLIQVFK | EFNFNLGEMN | KSNMKTD!IA | IGAWMVRGIG |
| 350 | IGGGFWP!LD | VK!KRSSIMV | LELTG!!QVV | WWIAGSMAQH | QSRGPASPLQ |
| 400 | PKRPQRLPGT | ISL!!DESHF | HFH!PGSFHE | YSLLLKHFNI | I!TEKDGLFL |
| 450 | VSCYMIAEIF | LLRLLWE!EI | VVLNSGTVQ! | MCL!LC!FAL | SMYNIQVCHP |
| 500 | NKRHIH!IVF | NPLTS!LFDP | HPHPRHFNSK | !REREELMNM | R!CSTGRMTF |
| 550 | Q!LKSISVPL | SLELLT!FDS | !CVYVLRLE! | CNFEYALIFQ | YSSYKCIRQL |
| 600 | EIIQSHVT!! | !GNILRNAL! | GDFIV!TSWS | ALIQT!MGHL | !PTQARWYSL |
| 650 | LLLGHTPVQH | VTALNTAGNC | NTVVSICVYK | HRKGTVKLWY | YNVMGPPSCK |
| 700 | WYVFDRNMVT | WFMTVYSLED | SQD!RHIRAN | !PL!HVIIVQ | LKTVDLSS |

SEQUENCE LISTING

<160> NUMBER OF SEQ ID NOS: 8

<210> SEQ ID NO 1

```
<211> LENGTH: 2222
<212> TYPE: DNA
<213> ORGANISM: Homo sapiens

<400> SEQUENCE: 1
atggggactg cagctgcggc agcggcggcg gcggcggcgg cggcggccgg ggaggggcg      60 cgtagcccga gccccgccgc cgtgtcgctc ggcctgggcg tggccgtcgt gtcgagcctg    120
gtgaacgggt ccacgttcgt gctacagaag aagggcatcg tgcgtgccaa gcggcgaggt    180
acttcctatt taacagacat tgtgtggtgg gctggcacaa tcgcaatggc tgttggccag    240
attggaaact tcctggctta cacggcggtc cccacggtcc tggtaacccc cctgggcgcc    300
cttggagtac cgttcgggtc cattttagct tcctatctcc tgaaggaaaa gctcaacatc    360
ttgggcaagt gggtgcct gctaagctgt gcaggctccg tcgtgctgat tatccactcc      420
ccaaagtctg agagtgtgac gactcaggct gagctggagg aaaagctgac caacccagtg    480
tttgtgggct acctgcat cgtgctgctc atgctgctgc tgctcatctt ctggatcgcg      540
ccggcccatg ggcccaccaa catcatggtc tacatcagca tctgctcctt gctgggcagt    600
ttcaccgtgc cttccaccaa gggcatcggg ctggcggccc aagacatctt gcataacaac    660
ccgtccagtc agagagccct ctgcctgtgc ctggtactcc tggccgtgct cggctgcagc    720
atcatcgtcc agttcaggta catcaacaag gcgctggagt gcttcgactc ctcggtgttc    780
ggggccatct actacgtcgt gtttaccacg ctggtcctgc tggcctcagc catcctcttc    840
cgggagtgga gcaacgtggg cctggtggac ttcttgggga tggcctgtgg attcacgacc    900
gtctccgtgg ggattgtcct tatacaggtg ttcaaagagt tcaattcaa ccttggggag     960 atgaacaaat ctaatatgaa acagactag attgcaatag gagcttggat ggttcgagga   1020
ataggcattg gaggtggttt ctggccgtga ttggatgtga agtagaagag gtcctcgatc   1080
atggtgttag aattgactgg atagtaacag gtggtctggt ggatagcggg gagcatggct   1140
cagcaccaga gcagaggccc agccagccct ctgcagccca acgtcccca acgggttgcct   1200 ggcaccatct ctctctgatg agacgaatct cattttcatt tccattaacc tggaagcttt   1260
catgaatatt ctcttctttt aaaacatttt aacattattt aaacagaaaa agatgggctc   1320
tttctggtta gttgttacat gatagcagag atattttac ttagattact ttgggaatga    1380
gagattgttg tcttgaactc tggcactgta cagtgaatgt gtctgtagtt gtgttagttt   1440
gcattaagca tgtataacat tcaagtatgt catccaaata gaggcatat acattgaatt    1500 gttttttaatc ctctgacaag ttgactcttc gaccccccacc cccacccaag acattttaat  1560
agtaaataga gagagagaga agagttaatg aacatgaggt agtgttccac tggcaggatg   1620
acttttcaat agctcaaatc aatttcagtg cctttatcac ttgaattatt aacttaattt   1680
gactcttaat gtgtatatgt tcttagatta gaataatgca acttcgagta tgctttaata   1740
tttcaatatt caagttacaa atgtataagg cagttagaaa taatacagtc acatgtcact   1800
taatgatagg gaaacattct gagaaatgca ttgtaaggtg acttatttgt gtgaacatca   1860
tggagtgcac ttatacaaac ctagatggga cacctatgac ccacccaggc cagatggtac   1920
agcctgttgc tcctgggcca cacacctgta cagcatgtga ccgcactgaa taccgcaggc   1980
aattgtaaca cagtggtgag tatttgtgtt tacaaacata ggaaaggtac agtaaaacta   2040
tggtattaca atgttatggg accaccgtca tgtaagtggt atgtctttga cagaaacatg   2100
gttacgtggt tcatgactgt atattcactg gaagatagtc aagactaaag acacattaga   2160
gcaaattgac ccctttaaca tgtgattatt gtccaattaa agacagttga tttaagtagc   2220
```

```
at                                                                   2222

<210> SEQ ID NO 2
<211> LENGTH: 2222
<212> TYPE: DNA
<213> ORGANISM: Homo sapiens

<400> SEQUENCE: 2
atggggactg cagctgcggc agcggcggcg gcggcggcgg cggcggccgg ggaggggggcg      60 cgtagcccga gccccgccgc cgtgtcgctc ggcctgggcg tggccgtcgt gtcgagcctg     120
gtgaacgggt ccaggttcgt gctacagaag aagggcatcg tgcgtgccaa gcggcgaggt     180
acttcctatt taacagacat tgtgtggtgg gctggcacaa tcgcaatggc tgttggccag     240
attggaaact tcctggctta cacggcggtc cccacggtcc tggtaacccc cctgggcgcc     300 cttgagtac cgttcgggtc cattttagct tcctatctcc tgaaggaaaa gctcaacatc     360
ttgggcaagt tggggtgcct gctaagctgt gcaggctccg tcgtgctgat tatccactcc     420
ccaaagtctg agagtgtgac gactcaggct gagctggagg aaaagctgac caacccagtg     480
tttgtgggct acctgtgcat cgtgctgctc atgctgctgc tgctcatctt ctggatcgcg     540
ccggcccatg ggcccaccaa catcatggtc tacatcagca tctgctcctt gctgggcagt     600
ttcaccgtgc cttccaccaa gggcatcggg ctggcggccc aagacatctt gcataacaac     660
ccgtccagtc agagagccct ctgcctgtgc ctggtactcc tggccgtgct cggctgcagc     720
atcatcgtcc agttcaggta catcaacaag gcgctggagt gcttcgactc ctcggtgttc     780
ggggccatct actacgtcgt gtttaccacg ctggtcctgc tggcctcagc catcctcttc     840
cgggagtgga gcaacgtggg cctggtggac ttcttgggga tggcctgtgg attcacgacc     900
gtctccgtgg ggattgtcct tatacaggtg ttcaaagagt tcaatttcaa ccttggggag     960
atgaacaaat ctaatatgaa aacagactag attgcaatag gagcttggat ggttcgagga    1020
ataggcattg gaggtggttt ctggccgtga ttggatgtga agtagaagag gtcctcgatc    1080
atggtgttag aattgactgg atagtaacag gtggtctggt ggatagcggg gagcatggct    1140
cagcaccaga gcagaggccc agccagccct ctgcagccca acgtccccca acggttgcct    1200
ggcaccatct ctctctgatg agacgaatct cattttcatt tccattaacc tggaagcttt    1260
catgaatatt ctcttctttt aaaacatttt aacattattt aaacagaaaa agatgggctc    1320
tttctggtta gttgttacat gatagcagag atatttttac ttagattact ttgggaatga    1380
gagattgttg tcttgaactc tggcactgta cagtgaatgt gtctgtagtt gtgttagttt    1440
gcattaagca tgtataacat tcaagtatgt catccaaata agaggcatat acattgaatt    1500
gtttttaatc ctctgacaag ttgactcttc gacccccacc cccacccaag acattttaat    1560 agtaaaataga gagagagaga agagttaatg aacatgaggt agtgttccac tggcaggatg    1620
acttttcaat agctcaaatc aatttcagtg cctttatcac ttgaattatt aacttaattt    1680
gactcttaat gtgtatatgt tcttagatta gaataatgca acttcgagta tgctttaata    1740
tttcaatatt caagttacaa atgtataagg cagttagaaa taatacagtc acatgtcact    1800
taatgatagg gaaacattct gagaaatgca ttgtaaggtg acttattgt gtgaacatca    1860 tggagtgcac ttatacaaac ctagatggga cacctatgac ccacccaggc cagatggtac    1920
agcctgttgc tcctgggcca cacacctgta cagcatgtga ccgcactgaa taccgcaggc    1980
aattgtaaca cagtggtgag tatttgtgtt tacaaacata ggaaaggtac agtaaaacta    2040
```

```
tggtattaca atgttatggg accaccgtca tgtaagtggt atgtctttga cagaaacatg    2100
gttacgtggt tcatgactgt atattcactg gaagatagtc aagactaaag acacattaga   2160
gcaaattgac ccctttaaca tgtgattatt gtccaattaa agacagttga tttaagtagc   2220
at                                                                  2222
```

<210> SEQ ID NO 3
<211> LENGTH: 329
<212> TYPE: PRT
<213> ORGANISM: Homo sapiens

<400> SEQUENCE: 3

```
Met Gly Thr Ala Ala Ala Ala Ala Ala Ala Ala Ala Ala Ala Ala
1               5                   10                  15

Gly Glu Gly Ala Arg Ser Pro Ser Pro Ala Ala Val Ser Leu Gly Leu
            20                  25                  30

Gly Val Ala Val Val Ser Ser Leu Val Asn Gly Ser Thr Phe Val Leu
        35                  40                  45

Gln Lys Lys Gly Ile Val Arg Ala Lys Arg Arg Gly Thr Ser Tyr Leu
    50                  55                  60

Thr Asp Ile Val Trp Trp Ala Gly Thr Ile Ala Met Ala Val Gly Gln
65                  70                  75                  80

Ile Gly Asn Phe Leu Ala Tyr Thr Ala Val Pro Thr Val Leu Val Thr
                85                  90                  95

Pro Leu Gly Ala Leu Gly Val Pro Phe Gly Ser Ile Leu Ala Ser Tyr
            100                 105                 110

Leu Leu Lys Glu Lys Leu Asn Ile Leu Gly Lys Leu Gly Cys Leu Leu
        115                 120                 125

Ser Cys Ala Gly Ser Val Val Leu Ile Ile His Ser Pro Lys Ser Glu
    130                 135                 140

Ser Val Thr Thr Gln Ala Glu Leu Glu Glu Lys Leu Thr Asn Pro Val
145                 150                 155                 160

Phe Val Gly Tyr Leu Cys Ile Val Leu Leu Met Leu Leu Leu Leu Ile
                165                 170                 175

Phe Trp Ile Ala Pro Ala His Gly Pro Thr Asn Ile Met Val Tyr Ile
            180                 185                 190

Ser Ile Cys Ser Leu Leu Gly Ser Phe Thr Val Pro Ser Thr Lys Gly
        195                 200                 205

Ile Gly Leu Ala Ala Gln Asp Ile Leu His Asn Asn Pro Ser Ser Gln
    210                 215                 220

Arg Ala Leu Cys Leu Cys Leu Val Leu Leu Ala Val Leu Gly Cys Ser
225                 230                 235                 240

Ile Ile Val Gln Phe Arg Tyr Ile Asn Lys Ala Leu Glu Cys Phe Asp
                245                 250                 255

Ser Ser Val Phe Gly Ala Ile Tyr Tyr Val Val Phe Thr Thr Leu Val
            260                 265                 270

Leu Leu Ala Ser Ala Ile Leu Phe Arg Glu Trp Ser Asn Val Gly Leu
        275                 280                 285

Val Asp Phe Leu Gly Met Ala Cys Gly Phe Thr Thr Val Ser Val Gly
    290                 295                 300

Ile Val Leu Ile Gln Val Phe Lys Glu Phe Asn Phe Asn Leu Gly Glu
305                 310                 315                 320

Met Asn Lys Ser Asn Met Lys Thr Asp
                325
```

<210> SEQ ID NO 4
<211> LENGTH: 329
<212> TYPE: PRT
<213> ORGANISM: Homo sapiens

<400> SEQUENCE: 4

```
Met Gly Thr Ala Ala Ala Ala Ala Ala Ala Ala Ala Ala Ala Ala
 1               5                  10                  15

Gly Glu Gly Ala Arg Ser Pro Ser Pro Ala Ala Val Ser Leu Gly Leu
                20                  25                  30

Gly Val Ala Val Val Ser Ser Leu Val Asn Gly Ser Arg Phe Val Leu
            35                  40                  45

Gln Lys Lys Gly Ile Val Arg Ala Lys Arg Arg Gly Thr Ser Tyr Leu
50                  55                  60

Thr Asp Ile Val Trp Trp Ala Gly Thr Ile Ala Met Ala Val Gly Gln
65                  70                  75                  80

Ile Gly Asn Phe Leu Ala Tyr Thr Ala Val Pro Thr Val Leu Val Thr
                85                  90                  95

Pro Leu Gly Ala Leu Gly Val Pro Phe Gly Ser Ile Leu Ala Ser Tyr
            100                 105                 110

Leu Leu Lys Glu Lys Leu Asn Ile Leu Gly Lys Leu Gly Cys Leu Leu
        115                 120                 125

Ser Cys Ala Gly Ser Val Val Leu Ile Ile His Ser Pro Lys Ser Glu
130                 135                 140

Ser Val Thr Thr Gln Ala Glu Leu Glu Glu Lys Leu Thr Asn Pro Val
145                 150                 155                 160

Phe Val Gly Tyr Leu Cys Ile Val Leu Leu Met Leu Leu Leu Leu Ile
                165                 170                 175

Phe Trp Ile Ala Pro Ala His Gly Pro Thr Asn Ile Met Val Tyr Ile
            180                 185                 190

Ser Ile Cys Ser Leu Leu Gly Ser Phe Thr Val Pro Ser Thr Lys Gly
        195                 200                 205

Ile Gly Leu Ala Ala Gln Asp Ile Leu His Asn Asn Pro Ser Ser Gln
210                 215                 220

Arg Ala Leu Cys Leu Cys Leu Val Leu Ala Val Leu Gly Cys Ser
225                 230                 235                 240

Ile Ile Val Gln Phe Arg Tyr Ile Asn Lys Ala Leu Glu Cys Phe Asp
                245                 250                 255

Ser Ser Val Phe Gly Ala Ile Tyr Tyr Val Val Phe Thr Thr Leu Val
            260                 265                 270

Leu Leu Ala Ser Ala Ile Leu Phe Arg Glu Trp Ser Asn Val Gly Leu
        275                 280                 285

Val Asp Phe Leu Gly Met Ala Cys Gly Phe Thr Thr Val Ser Val Gly
290                 295                 300

Ile Val Leu Ile Gln Val Phe Lys Glu Phe Asn Leu Gly Glu
305                 310                 315                 320

Met Asn Lys Ser Asn Met Lys Thr Asp
                325
```

<210> SEQ ID NO 5
<211> LENGTH: 2247
<212> TYPE: DNA
<213> ORGANISM: Homo sapiens

<400> SEQUENCE: 5

```
ggctcggagg gcgggcgcgg gcggaatggg gactgcagct gcggcagcgg cggcggcggc      60
ggcggcggcg gccggggagg gggcgcgtag cccgagcccc gccgccgtgt cgctcggcct     120
gggcgtggcc gtcgtgtcga gcctggtgaa cgggtccacg ttcgtgctac agaagaaggg     180
catcgtgcgt gccaagcggc gaggtacttc ctatttaaca acattgtgt ggtgggctgg      240
cacaatcgca atggctgttg gccagattgg aaacttcctg gcttacacgg cggtccccac     300
ggtcctggta accccctgg gcgcccttgg agtaccgttc gggtccattt tagcttccta      360
tctcctgaag gaaaagctca acatcttggg caagttgggg tgcctgctaa gctgtgcagg     420
ctccgtcgtg ctgattatcc actccccaaa gtctgagagt gtgacgactc aggctgagct     480
ggaggaaaag ctgaccaacc cagtgtttgt gggctacctg tgcatcgtgc tgctcatgct     540
gctgctgctc atcttctgga tcgcgccggc ccatgggccc accaacatca tggtctacat     600
cagcatctgc tccttgctgg gcagtttcac cgtgccttcc accaagggca tcgggctggc     660
ggcccaagac atcttgcata caacccgtc cagtcagaga gccctctgcc tgtgcctggt      720
actcctggcc gtgctcggct gcagcatcat cgtccagttc aggtacatca acaaggcgct     780
ggagtgcttc gactcctcgg tgttcggggc catctactac gtcgtgttta ccacgctggt     840
cctgctggcc tcagccatcc tcttccggga gtggagcaac gtgggcctgg tggacttctt     900
ggggatggcc tgtggattca cgaccgtctc cgtggggatt gtccttatac aggtgttcaa     960
agagttcaat ttcaaccttg gggagatgaa caaatctaat atgaaaacag actagattgc    1020
aataggagct tggatggttc gaggaatagg cattggaggt ggtttctggc cgtgattgga    1080
tgtgaagtag aagaggtcct cgatcatggt gttagaattg actggatagt aacaggtggt    1140
ctggtggata gcggggagca tggctcagca ccagagcaga ggcccagcca gccctctgca    1200
gcccaaacgt ccccaacggt tgcctggcac catctctctc tgatgagacg aatctcattt    1260
tcatttccat taacctggaa gctttcatga atattctctt cttttaaaac atttttaacat   1320
tatttaaaca gaaaaagatg ggctctttct ggttagttgt tacatgatag cagagatatt    1380
tttacttaga ttactttggg aatgagagat tgttgtcttg aactctggca ctgtacagtg    1440
aatgtgtctg tagttgtgtt agtttgcatt aagcatgtat aacattcaag tatgtcatcc    1500
aaataagagg catatacatt gaattgtttt taatcctctg acaagttgac tcttcgaccc    1560
ccaccccac ccaagacatt ttaatagtaa atagagagag agaagagt taatgaacat       1620
gaggtagtgt tccactggca ggatgacttt tcaatagctc aaatcaattt cagtgccttt    1680
atcacttgaa ttattaactt aatttgactc ttaatgtgta tatgttctta gattagaata    1740
atgcaacttc gagtatgctt taatatttca atattcaagt tacaaatgta taaggcagtt    1800
agaaataata cagtcacatg tcacttaatg atagggaaac attctgagaa atgcattgta    1860
aggtgacttt attgtgtgaa catcatggag tgcacttata caaacctaga tgggacacct    1920
atgacccacc caggccagat ggtacagcct gttgctcctg ggccacacac ctgtacagca    1980
tgtgaccgca ctgaataccg caggcaattg taacacagtg gtgagtattt gtgtttacaa    2040
acataggaaa ggtacagtaa aactatggta ttacaatgtt atgggaccac cgtcatgtaa    2100
gtggtatgtc tttgacagaa acatggttac gtggttcatg actgtatatt cactggaaga   2160
tagtcaagac taaagacaca ttagagcaaa ttgaccccctt taacatgtga ttattgtcca    2220
attaaagaca gttgatttaa gtagcat                                         2247
```

<210> SEQ ID NO 6
<211> LENGTH: 2247

<212> TYPE: DNA
<213> ORGANISM: Homo sapiens

<400> SEQUENCE: 6

| | | | | | |
|---|---|---|---|---|---|
| ggctcggagg | gcgggcgcgg | gcggaatggg | gactgcagct | gcggcagcgg | cggcggcggc | 60 |
| ggcggcggcg | gccggggagg | gggcgcgtag | cccgagcccc | gccgccgtgt | cgctcggcct | 120 |
| gggcgtggcc | gtcgtgtcga | gcctggtgaa | cgggtccagg | ttcgtgctac | agaagaaggg | 180 |
| catcgtgcgt | gccaagcggc | gaggtacttc | ctatttaaca | gacattgtgt | ggtgggctgg | 240 |
| cacaatcgca | atggctgttg | gccagattgg | aaacttcctg | gcttacacgg | cggtccccac | 300 |
| ggtcctggta | accccctgg | gcgcccttgg | agtaccgttc | gggtccattt | tagcttccta | 360 |
| tctcctgaag | gaaaagctca | acatcttggg | caagttgggg | tgcctgctaa | gctgtgcagg | 420 |
| ctccgtcgtg | ctgattatcc | actccccaaa | gtctgagagt | gtgacgactc | aggctgagct | 480 |
| ggaggaaaag | ctgaccaacc | cagtgtttgt | gggctacctg | tgcatcgtgc | tgctcatgct | 540 |
| gctgctgctc | atcttctgga | tcgcgccggc | ccatgggccc | accaacatca | tggtctacat | 600 |
| cagcatctgc | tccttgctgg | gcagtttcac | cgtgccttcc | accaagggca | tcgggctggc | 660 |
| ggcccaagac | atcttgcata | caacccgtc | cagtcagaga | gccctctgcc | tgtgcctggt | 720 |
| actcctggcc | gtgctcggct | gcagcatcat | cgtccagttc | aggtacatca | acaaggcgct | 780 |
| ggagtgcttc | gactcctcgg | tgttcggggc | catctactac | gtcgtgttta | ccacgctggt | 840 |
| cctgctggcc | tcagccatcc | tcttccggga | gtggagcaac | gtgggcctgg | tggacttctt | 900 |
| ggggatggcc | tgtggattca | cgaccgtctc | cgtggggatt | gtccttatac | aggtgttcaa | 960 |
| agagttcaat | ttcaaccttg | gggagatgaa | caaatctaat | atgaaaacag | actagattgc | 1020 |
| aataggagct | tggatggttc | gaggaatagg | cattggaggg | ggtttctggc | cgtgattgga | 1080 |
| tgtgaagtag | aagaggtcct | cgatcatggt | gttagaattg | actggatagt | aacaggtggt | 1140 |
| ctggtggata | gcggggagca | tggctcagca | ccagagcaga | ggcccagcca | gccctctgca | 1200 |
| gcccaaacgt | ccccaacggt | tgcctggcac | catctctctc | tgatgagacg | aatctcattt | 1260 |
| tcatttccat | taacctggaa | gctttcatga | atattctctt | cttttaaaac | attttaacat | 1320 |
| tatttaaaca | gaaaaagatg | ggctctttct | ggttagttgt | tacatgatag | cagagatatt | 1380 |
| tttacttaga | ttacttttggg | aatgagagat | tgttgtcttg | aactctggca | ctgtacagtg | 1440 |
| aatgtgtctg | tagttgtgtt | agtttgcatt | aagcatgtat | aacattcaag | tatgtcatcc | 1500 |
| aaataagagg | catatacatt | gaattgtttt | taatcctctg | acaagttgac | tcttcgaccc | 1560 |
| ccaccccac | ccaagacatt | taatagtaa | atagagagag | agagaagagt | taatgaacat | 1620 |
| gaggtagtgt | tccactggca | ggatgacttt | tcaatagctc | aaatcaattt | cagtgccttt | 1680 |
| atcacttgaa | ttattaactt | aatttgactc | ttaatgtgta | tatgttctta | gattagaata | 1740 |
| atgcaacttc | gagtatgctt | taatatttca | atattcaagt | tacaaatgta | taaggcagtt | 1800 |
| agaaataata | cagtcacatg | tcacttaatg | atagggaaac | attctgagaa | atgcattgta | 1860 |
| aggtgacttt | attgtgtgaa | catcatggag | tgcacttata | caaacctaga | tgggacacct | 1920 |
| atgacccacc | caggccagat | ggtacagcct | gttgctcctg | ggccacacac | ctgtacagca | 1980 |
| tgtgaccgca | ctgaataccg | caggcaattg | taacacagtg | gtgagtattt | tgtttacaa | 2040 |
| acataggaaa | ggtacagtaa | aactatggta | ttacaatgtt | atgggaccac | cgtcatgtaa | 2100 |
| gtggtatgtc | tttgacagaa | acatggttac | gtggttcatg | actgtatatt | cactggaaga | 2160 |
| tagtcaagac | taaagacaca | ttagagcaaa | ttgaccccctt | taacatgtga | ttattgtcca | 2220 | attaaagaca gttgatttaa gtagcat 2247

<210> SEQ ID NO 7
<211> LENGTH: 717
<212> TYPE: PRT
<213> ORGANISM: Homo sapiens

<400> SEQUENCE: 7

```
Ala Arg Arg Ala Gly Ala Gly Gly Met Gly Thr Ala Ala Ala Ala
1               5                   10                  15

Ala Ala Ala Ala Ala Ala Ala Gly Glu Gly Ala Arg Ser Pro Ser
                20                  25                  30

Pro Ala Ala Val Ser Leu Gly Leu Gly Val Ala Val Val Ser Ser Leu
            35                  40                  45

Val Asn Gly Ser Thr Phe Val Leu Gln Lys Lys Gly Ile Val Arg Ala
        50                  55                  60

Lys Arg Arg Gly Thr Ser Tyr Leu Thr Asp Ile Val Trp Trp Ala Gly
65                  70                  75                  80

Thr Ile Ala Met Ala Val Gly Gln Ile Gly Asn Phe Leu Ala Tyr Thr
                85                  90                  95

Ala Val Pro Thr Val Leu Val Thr Pro Leu Gly Ala Leu Gly Val Pro
            100                 105                 110

Phe Gly Ser Ile Leu Ala Ser Tyr Leu Leu Lys Glu Lys Leu Asn Ile
        115                 120                 125

Leu Gly Lys Leu Gly Cys Leu Leu Ser Cys Ala Gly Ser Val Val Leu
    130                 135                 140

Ile Ile His Ser Pro Lys Ser Glu Ser Val Thr Thr Gln Ala Glu Leu
145                 150                 155                 160

Glu Glu Lys Leu Thr Asn Pro Val Phe Val Gly Tyr Leu Cys Ile Val
                165                 170                 175

Leu Leu Met Leu Leu Leu Ile Phe Trp Ile Ala Pro Ala His Gly
            180                 185                 190

Pro Thr Asn Ile Met Val Tyr Ile Ser Ile Cys Ser Leu Leu Gly Ser
        195                 200                 205

Phe Thr Val Pro Ser Thr Lys Gly Ile Gly Leu Ala Ala Gln Asp Ile
    210                 215                 220

Leu His Asn Asn Pro Ser Ser Gln Arg Ala Leu Cys Leu Cys Leu Val
225                 230                 235                 240

Leu Leu Ala Val Leu Gly Cys Ser Ile Ile Val Gln Phe Arg Tyr Ile
                245                 250                 255

Asn Lys Ala Leu Glu Cys Phe Asp Ser Ser Val Phe Gly Ala Ile Tyr
            260                 265                 270

Tyr Val Val Phe Thr Thr Leu Val Leu Leu Ala Ser Ala Ile Leu Phe
        275                 280                 285

Arg Glu Trp Ser Asn Val Gly Leu Val Asp Phe Leu Gly Met Ala Cys
    290                 295                 300

Gly Phe Thr Thr Val Ser Val Gly Ile Val Leu Ile Gln Val Phe Lys
305                 310                 315                 320

Glu Phe Asn Phe Asn Leu Gly Glu Met Asn Lys Ser Asn Met Lys Thr
                325                 330                 335

Asp Ile Ala Ile Gly Ala Trp Met Val Arg Gly Ile Gly Ile Gly Gly
            340                 345                 350

Gly Phe Trp Pro Leu Asp Val Lys Lys Arg Ser Ser Ile Met Val Leu
        355                 360                 365
```

```
Glu Leu Thr Gly Gln Val Val Trp Trp Ile Ala Gly Ser Met Ala Gln
    370                 375                 380

His Gln Ser Arg Gly Pro Ala Ser Pro Leu Gln Pro Lys Arg Pro Gln
385                 390                 395                 400

Arg Leu Pro Gly Thr Ile Ser Leu Asp Glu Ser His Phe His Phe His
                405                 410                 415

Pro Gly Ser Phe His Glu Tyr Ser Leu Leu Lys His Phe Asn Ile
            420                 425                 430

Ile Thr Glu Lys Asp Gly Leu Phe Leu Val Ser Cys Tyr Met Ile Ala
                435                 440                 445

Glu Ile Phe Leu Leu Arg Leu Leu Trp Glu Ile Val Val Leu Asn
    450                 455                 460

Ser Gly Thr Val Gln Met Cys Leu Leu Cys Phe Ala Leu Ser Met Tyr
465                 470                 475                 480

Asn Ile Gln Val Cys His Pro Asn Lys Arg His Ile His Ile Val Phe
                485                 490                 495

Asn Pro Leu Thr Ser Leu Phe Asp Pro His Pro His Pro Arg His Phe
            500                 505                 510

Asn Ser Lys Arg Glu Arg Glu Glu Leu Met Asn Met Arg Cys Ser Thr
    515                 520                 525

Gly Arg Met Thr Phe Gln Leu Lys Ser Ile Ser Val Pro Leu Ser Leu
530                 535                 540

Glu Leu Leu Thr Phe Asp Ser Cys Val Tyr Val Leu Arg Leu Glu Cys
545                 550                 555                 560

Asn Phe Glu Tyr Ala Leu Ile Phe Gln Tyr Ser Ser Tyr Lys Cys Ile
                565                 570                 575

Arg Gln Leu Glu Ile Ile Gln Ser His Val Thr Gly Asn Ile Leu Arg
            580                 585                 590

Asn Ala Leu Gly Asp Phe Ile Val Thr Ser Trp Ser Ala Leu Ile Gln
    595                 600                 605

Thr Met Gly His Leu Pro Thr Gln Ala Arg Trp Tyr Ser Leu Leu Leu
610                 615                 620

Leu Gly His Thr Pro Val Gln His Val Thr Ala Leu Asn Thr Ala Gly
625                 630                 635                 640

Asn Cys Asn Thr Val Val Ser Ile Cys Val Tyr Lys His Arg Lys Gly
                645                 650                 655

Thr Val Lys Leu Trp Tyr Tyr Asn Val Met Gly Pro Pro Ser Cys Lys
            660                 665                 670

Trp Tyr Val Phe Asp Arg Asn Met Val Thr Trp Phe Met Thr Val Tyr
    675                 680                 685

Ser Leu Glu Asp Ser Gln Asp Arg His Ile Arg Ala Asn Pro Leu His
    690                 695                 700

Val Ile Ile Val Gln Leu Lys Thr Val Asp Leu Ser Ser
705                 710                 715

<210> SEQ ID NO 8
<211> LENGTH: 717
<212> TYPE: PRT
<213> ORGANISM: Homo sapiens

<400> SEQUENCE: 8

Ala Arg Arg Ala Gly Ala Gly Met Gly Thr Ala Ala Ala Ala Ala
1               5                   10                  15

Ala Ala Ala Ala Ala Ala Ala Gly Glu Gly Ala Arg Ser Pro Ser
                20                  25                  30
```

```
Pro Ala Ala Val Ser Leu Gly Leu Gly Val Ala Val Val Ser Ser Leu
            35                  40                  45

Val Asn Gly Ser Arg Phe Val Leu Gln Lys Lys Gly Ile Val Arg Ala
 50                  55                  60

Lys Arg Gly Thr Ser Tyr Leu Thr Asp Ile Val Trp Trp Ala Gly
 65              70                  75                  80

Thr Ile Ala Met Ala Val Gly Gln Ile Gly Asn Phe Leu Ala Tyr Thr
                85                  90                  95

Ala Val Pro Thr Val Leu Val Thr Pro Leu Gly Ala Leu Gly Val Pro
            100                 105                 110

Phe Gly Ser Ile Leu Ala Ser Tyr Leu Leu Lys Glu Lys Leu Asn Ile
            115                 120                 125

Leu Gly Lys Leu Gly Cys Leu Ser Cys Ala Gly Ser Val Val Leu
    130                 135                 140

Ile Ile His Ser Pro Lys Ser Glu Ser Val Thr Thr Gln Ala Glu Leu
145                 150                 155                 160

Glu Glu Lys Leu Thr Asn Pro Val Phe Val Gly Tyr Leu Cys Ile Val
                165                 170                 175

Leu Leu Met Leu Leu Leu Ile Phe Trp Ile Ala Pro Ala His Gly
            180                 185                 190

Pro Thr Asn Ile Met Val Tyr Ile Ser Ile Cys Ser Leu Leu Gly Ser
            195                 200                 205

Phe Thr Val Pro Ser Thr Lys Gly Ile Gly Leu Ala Ala Gln Asp Ile
    210                 215                 220

Leu His Asn Asn Pro Ser Ser Gln Arg Ala Leu Cys Leu Cys Leu Val
225                 230                 235                 240

Leu Leu Ala Val Leu Gly Cys Ser Ile Ile Val Gln Phe Arg Tyr Ile
                245                 250                 255

Asn Lys Ala Leu Glu Cys Phe Asp Ser Ser Val Phe Gly Ala Ile Tyr
            260                 265                 270

Tyr Val Val Phe Thr Thr Leu Val Leu Leu Ala Ser Ala Ile Leu Phe
    275                 280                 285

Arg Glu Trp Ser Asn Val Gly Leu Val Asp Phe Leu Gly Met Ala Cys
290                 295                 300

Gly Phe Thr Thr Val Ser Val Gly Ile Val Leu Ile Gln Val Phe Lys
305                 310                 315                 320

Glu Phe Asn Phe Asn Leu Gly Glu Met Asn Lys Ser Asn Met Lys Thr
                325                 330                 335

Asp Ile Ala Ile Gly Ala Trp Met Val Arg Gly Ile Gly Ile Gly Gly
            340                 345                 350

Gly Phe Trp Pro Leu Asp Val Lys Lys Arg Ser Ser Ile Met Val Leu
    355                 360                 365

Glu Leu Thr Gly Gln Val Val Trp Trp Ile Ala Gly Ser Met Ala Gln
    370                 375                 380

His Gln Ser Arg Gly Pro Ala Ser Pro Leu Gln Pro Lys Arg Pro Gln
385                 390                 395                 400

Arg Leu Pro Gly Thr Ile Ser Leu Asp Glu Ser His Phe His Phe His
                405                 410                 415

Pro Gly Ser Phe His Glu Tyr Ser Leu Leu Leu Lys His Phe Asn Ile
            420                 425                 430

Ile Thr Glu Lys Asp Gly Leu Phe Leu Val Ser Cys Tyr Met Ile Ala
            435                 440                 445
```

-continued

```
Glu Ile Phe Leu Leu Arg Leu Leu Trp Glu Glu Ile Val Val Leu Asn
    450                 455                 460

Ser Gly Thr Val Gln Met Cys Leu Leu Cys Phe Ala Leu Ser Met Tyr
465                 470                 475                 480

Asn Ile Gln Val Cys His Pro Asn Lys Arg His Ile His Ile Val Phe
                485                 490                 495

Asn Pro Leu Thr Ser Leu Phe Asp Pro His Pro His Pro Arg His Phe
                500                 505                 510

Asn Ser Lys Arg Glu Arg Glu Glu Leu Met Asn Met Arg Cys Ser Thr
        515                 520                 525

Gly Arg Met Thr Phe Gln Leu Lys Ser Ile Ser Val Pro Leu Ser Leu
        530                 535                 540

Glu Leu Leu Thr Phe Asp Ser Cys Val Tyr Val Leu Arg Leu Glu Cys
545                 550                 555                 560

Asn Phe Glu Tyr Ala Leu Ile Phe Gln Tyr Ser Ser Tyr Lys Cys Ile
                565                 570                 575

Arg Gln Leu Glu Ile Ile Gln Ser His Val Thr Gly Asn Ile Leu Arg
                580                 585                 590

Asn Ala Leu Gly Asp Phe Ile Val Thr Ser Trp Ser Ala Leu Ile Gln
        595                 600                 605

Thr Met Gly His Leu Pro Thr Gln Ala Arg Trp Tyr Ser Leu Leu Leu
        610                 615                 620

Leu Gly His Thr Pro Val Gln His Val Thr Ala Leu Asn Thr Ala Gly
625                 630                 635                 640

Asn Cys Asn Thr Val Val Ser Ile Cys Val Tyr Lys His Arg Lys Gly
                645                 650                 655

Thr Val Lys Leu Trp Tyr Tyr Asn Val Met Gly Pro Pro Ser Cys Lys
                660                 665                 670

Trp Tyr Val Phe Asp Arg Asn Met Val Thr Trp Phe Met Thr Val Tyr
                675                 680                 685

Ser Leu Glu Asp Ser Gln Asp Arg His Ile Arg Ala Asn Pro Leu His
        690                 695                 700

Val Ile Ile Val Gln Leu Lys Thr Val Asp Leu Ser Ser
705                 710                 715
```

COMPOSITIONS AND METHODS FOR DETECTING AND TREATING NEUROLOGICAL CONDITIONS

This application claims priority to U.S. Provisional Application Ser. No. 60/496,317, filed Aug. 19, 2003, which is hereby incorporated by reference in its entirety.

This invention was made with government support under Grants Nos. NS33645, NS38713, ES10631 awarded by the National Institutes of Health. The Government has certain rights in the invention.

FIELD OF THE INVENTION

The present invention relates to the NIPA-1 proteins and nucleic acids encoding the NIPA-1 proteins. The present invention further provides assays for the detection of NIPA-1 polymorphisms and mutations associated with disease states, as well as methods of screening for therapeutic agents, ligands, and modulators of NIPA-1 proteins.

BACKGROUND OF THE INVENTION

Hereditary spastic paraplegia (HSP) (also known as Familial Spastic Paraparesis and Strumpell-Lorrain syndrome) is not a single disease entity but rather a group of clinically and genetically diverse disorders that share the primary feature of progressive, generally severe, lower extremity spasticity. HSP is classified as "uncomplicated" (symptoms confined to lower extremity weakness, bladder disturbance, and to a lesser extent impaired position sense in the legs); and "complicated" when additional neurologic deficits are present.

Following normal gestation, delivery, and early childhood development, subjects with uncomplicated autosomal dominant HSP develop leg stiffness and gait disturbance (e.g., stumbling and tripping) due to difficulty dorsiflexing the foot and weakness of hip flexion. Although the majority of patients experience symptom onset in the second through fourth decades, there is a wide range of age of symptom onset (from infancy through age 85) (Cooley et al, Clin Gen 38:57-68 (1990); Durr et al, Neurology 44:1274-7 (1994); Hazan et al, Nat Genet 5:163-7 (1993)). Gait disturbance progresses insidiously without exacerbations, remissions, or step-wise worsening. Paresthesiae below the knees are not uncommon. Urinary urgency progressing to urinary incontinence is a frequent, although variable, late manifestation.

Neurologic examination of subjects with uncomplicated HSP reveals normal facial and extraocular movements and normal fundi. Although jaw jerk may be brisk in older subjects, there is no speech disturbance, difficulty swallowing or evidence of frank corticobulbar tract dysfunction. Upper extremity muscle tone and strength are normal. In the lower extremities, muscle tone is increased at the hamstrings, quadriceps and ankles. Weakness is most notable at the iliopsoas, tibialis anterior, and to a lesser extent, hamstring muscles. Muscle wasting may occur in uncomplicated HSP (Harding A E, J Neurol Neurosurg Psychiatry 44:871-83 (1981); Silver J R, J Neurol Neurosurg Psychiatry 29:135-44 (1996); Cross et al, Arch Neurol 16:473-85 (1967); Refsum and Skillicorn, Neurology 4:40-7 (1954)). Peripheral nerves are normal in uncomplicated HSP although decreased perception of sharp stimuli below the knees is noted occasionally. Vibratory sense is often diminished mildly in the distal lower extremities. When present, this is a useful diagnostic sign that helps distinguish HSP from other disorders. Slight terminal dysmetria is observed occasionally on finger-to-nose testing in older affected subjects. Deep tendon reflexes may be brisk in the upper extremities but are pathologically increased in the lower extremities. Gait demonstrates circumduction owing to difficulty with hip flexion and ankle dorsiflexion. Crossed adductor reflexes, ankle clonus, and extensor plantar responses are present uniformly. Hoffman's and Tromner's signs may be observed. High arched feet (pes cavus) are generally present and usually prominent in older affected subjects.

The age of symptom onset, rate of symptom progression, and extent of disability are variable both within and between HSP kindreds (Durr et al, Neurology 44:1274-7 (1994); Schady and Scheard, Brain 113:709-20 (1990); Polo et al, J Neurol Neurosurg Psychiatry 56:175-81 (1993); Holmes and Shaywitz, J Neurol Neurosurg Psychiatry 40:1003-8 (1977)). In contrast to variable age of symptom onset and extent of disability, the distribution of neurologic deficits in uncomplicated HSP is invariant and consist of spastic weakness in the legs; variable impairment of vibratory sense in the feet; and variable urinary bladder disturbance. Additional deficits such as visual disturbance, marked muscle wasting, fasciculations, dementia, seizures, or peripheral neuropathy in subjects from uncomplicated HSP kindreds should not be attributed to variant presentations of uncomplicated HSP. Rather, such subjects should be evaluated thoroughly for concurrent or alternative neurologic disorders. Some autosomal dominant uncomplicated HSP kindreds that exhibit onset of progressive spastic paraplegia in childhood (before age 6 years) and relatively little progression of symptoms beyond adolescence. These patients often do not experience urinary bladder disturbances and generally remain ambulatory (with assistance).

Electrophysiologic studies are useful for assessing peripheral nerve, muscle, dorsal column, and corticospinal tract involvement in HSP (Harding A E, Semin Neurol 13:333-6 (1993)). These studies are particularly useful for characterizing the extent of involvement since autopsies are obtained infrequently. Although results of these studies are variable, a number of generalizations can be made. Most studies found nerve conduction studies to be normal (in contrast to Friedrich's ataxia and some other spinocerebellar ataxias) (Rosenberg R N, Arch Neurol 50:1123-8 (1993)). One study however, showed that subclinical sensory impairment was common in HSP, with involvement of peripheral nerves, spinal pathways, or both (Schady and Scheard, Brain 113: 709-20 (1990)). Lower extremity somatosensory evoked potentials (SSEP) show conduction delay in dorsal column fibers (Pelosi et al, J Neurol Neurosurg Psychiatry 54:1099-102 (1991)). Cortical evoked potentials used to measure neurotransmission in corticospinal tracts show greatly reduced corticospinal tract conduction velocity and amplitude of evoked potential (Claus et al, Ann Neurol 28:43-9 (1990); Polo et al, J Neurol Neurosurg Psychiatry 56:175-81 (1993); Schady et al, J Neurol Neurosurg Psychiatry 54:775-9 (1991); Pelosi et al, J Neurol Neurosurg Psychiatry 54:1099-102 (1991)). Often, there is no cortical evoked potential elicited in muscles innervated by lumbar spinal segments, but cortical evoked potentials of the arms are normal or show only mildly reduced conduction velocity. These findings indicate that there are decreased numbers of corticospinal tract axons reaching the lumbar spinal cord and that the remaining axons have reduced conduction velocity. Central motor conduction velocity in the upper extremities was normal except for all 5 (affected) members of one HSP kindred for whom responses were considerably delayed.

Measurement of central motor conduction velocity may be a useful way of identifying clinical subgroups of HSP.

Currently, there is no specific treatment to prevent, retard, or reverse HSP's progressive disability. Treatments aimed at reducing and preventing HSP symptoms are needed. In addition, the molecular pathogenesis of HSP is poorly understood. As such, an understanding of the molecular pathogenesis surrounding HSP and similar disorders is also needed.

SUMMARY OF THE INVENTION

The present invention relates to the NIPA-1 proteins and nucleic acids encoding the NIPA-1 proteins. The present invention further provides assays for the detection of NIPA-1 polymorphisms and mutations associated with disease states, as well as methods of screening for therapeutic agents, ligands and modulators of NIPA-1 proteins.

Accordingly, in some embodiments, the present invention provides a composition comprising an isolated and purified nucleic acid sequence encoding a protein selected from the group consisting of SEQ ID NOs: 3 and 4. In some embodiments, the sequence is operably linked to a heterologous promoter. In other embodiments, the sequence is contained within a vector. In further embodiments, the vector is within a host cell.

In still other embodiments, the nucleic acid is selected from the group consisting of SEQ ID NO: 1 and variants thereof that are at least 80% identical to SEQ ID NO: 2. In some embodiments, the nucleic acid sequence is selected from the group consisting of SEQ ID NOs: 1 and 2.

The present invention also provides a composition comprising a polypeptide having an amino acid sequence selected from the group consisting of SEQ ID NOs: 3 and 4 and variants thereof that are at least 80% identical to SEQ ID NOs: 3 and 4. In some embodiments, the polypeptide is at least 90% identical to SEQ ID NOs: 3 and 4. In other embodiments, the polypeptide is at least 95% identical to SEQ ID NOs: 3 and 4. In still other embodiments, the polypeptide is selected from the group consisting of SEQ ID NOs: 3 and 4.

The present invention also provides a method of reducing NIPA-1 activity comprising providing a target cell expressing NIPA-1 protein, and an agent that inhibits NIPA-1, and contacting the target cell with the composition thereby reducing NIPA-1 activity. In some embodiments, the contacting is conducted in vitro. In some embodiments, the agent comprises a composition comprising a small interfering RNA duplex (siRNA), or a vector encoding said siRNA, that targets the NIPA-1 mRNA. In other embodiments, the target cell is a neurological cell. In further embodiments, the contacting is conducted under conditions such that the vector expresses the siRNA in the target cell. In still other embodiments, the composition further comprises a nucleic acid transfecting agent.

The present invention also provides a method comprising providing a subject with symptoms of hereditary spastic paraplegia, and an agent that reduces symptoms of hereditary spastic paraplegia, and administering the agent to the subject under conditions such that one or more symptoms of the hereditary spastic paraplegia are reduced. In preferred embodiments, the agent comprises a composition comprising small interfering RNA duplexes (siRNAs), or vectors encoding said siRNAs, configured to inhibit expression of NIPA-1 protein. In further embodiments, the hereditary spastic paraplegia is autosomal dominant hereditary spastic paraplegia. In other embodiments, the agent is administered intravenous, topically, and orally. In still further embodiments, the composition further comprises a nucleic acid transfecting agent. In still further embodiments, the composition further comprises reagents suitable for topcial administration.

The present invention also provides a method comprising providing a subject at risk for hereditary spastic paraplegia, and an agent that reduces symptoms of hereditary spastic paraplegia, and administering the agent to the subject under conditions such that one or more symptoms of the hereditary spastic paraplegia are prevented. In preferred embodiments, the agent comprises a composition comprising small interfering RNA duplexes (siRNAs), or a vector encoding said siRNA, configured to inhibit expression of NIPA-1 protein. In some embodiments, the hereditary spastic paraplegia is autosomal dominant hereditary spastic paraplegia. In other embodiments, the agent is administered intravenous, topically, and orally. In still further embodiments, the composition further comprises a nucleic acid transfecting agent. In still further embodiments, the composition further comprises reagents suitable for topcial administration.

The present invention further provides a composition comprising a composition comprising small interfering RNA duplexes (siRNAs), or vectors encoding said siRNA, configured to inhibit expression of NIPA-1 protein, and a nucleic acid transfecting agent.

The present invention also provides a kit comprising a composition, wherein said composition inhibits expression of NIPA-1 protein, and printed material with instructions for employing said composition for treating a target cell expressing NIPA-1 protein via expression of NIPA-1 mRNA under conditions such that the NIPA-1 mRNA is cleaved. In further embodiments, the composition comprises small interfering RNA duplexes (siRNAs), or vector encoding said siRNAs, configured to inhibit expression of NIPA-1 protein.

The present invention also provides a method for producing variants of NIPA-1 comprising providing a nucleic acid sequence selected from the group consisting of SEQ ID NOs: 1 and 2, mutagenizing the nucleic acid sequence, and screening the variant for NIPA-1 activity.

The present invention further provides a method for screening compounds for the ability to alter NIPA-1 activity comprising providing a polypeptide sequence comprising at least a portion of NIPA-1, one or more test compounds, and combining in any order, the polypeptide sequence comprising at least a portion of NIPA-1, and the one or more test compounds under conditions such that the polypeptide sequence, and the test compound interact, and measuring NIPA-1 activity.

The present invention further provides a method for identifying pharmaceutical agents useful for treating hereditary spastic paraplegias, comprising providing target cells, wherein the target cells comprise NIPA-1 polypeptide, and a candidate pharmaceutical agent, and exposing the target cells to the candidate pharmaceutical agents, measuring the activity of said NIPA-1 polypeptide of said target cells, and selecting candidate pharmaceutical agents that inhibit the activity of the NIPA-1 polypeptide. In other embodiments, the method is used for identifying hereditary spastic paraplegias, and other motor neuron diseases including, but not limited to, amyotrophic lateral sclerosis and primary lateral sclerosis, and other neurologic disorders, including, but not limited to, spinal chord injury, peripheral nerve disorders, and cerebal palsy.

The present invention also provides a method for diagnosing hereditary spastic paraplegia, comprising detecting the presence or absence of a polymorphism associated with NIPA-1 gene in a sample. In some embodiments, the polymorphism is in the coding region of said NIPA-1 gene. In further embodiments, the polymorphism is a C to G change at postion 159. In still further embodiments, the polymorphism is in linkage disequilibrium with a C to G change at position 159. In other embodiments, the polyporphic protein comprises additional NIPA-1 amino acid changes.

In other embodiments, the polymorphism disturbs NIPA-1 mRNA composition or stability. In other preferred embodiments, the polymorphism alters NIPA-1 protein sequence including amino acid substitutions, premature protein termination, and aberrant NIPA-1 mRNA splicing leading to altered NIPA-1 protein sequence.

In other embodiments, the detecting comprises detecting the polymorphism in a nucleic acid from said sample. In further embodiments, the sample is DNA. In other embodiments, the sample is RNA.

In further embodiments, the detecting comprises detecting a polymorphic protein. In still further embodiments, the detecting a polymorphic protein occurs with an antibody. In yet other embodiments, the polymorphic protein comprises amino acid change threonine to arginine at position 45.

The present invention also provides a method for diagnosing hereditary spastic paraplegia, comprising detecting the presence or absence of a NIPA-1 gene sequence variation in a sample. In some embodiments, the NIPA-1 gene sequence variation is in the coding region of said NIPA-1 gene. In further embodiments, the NIPA-1 gene sequence variation is a C to G change at postion 159. In still further embodiments, the NIPA-1 gene sequence variation is in linkage disequilibrium with a C to G change at position 159.

In other embodiments, the NIPA-1 gene sequence variation disturbs NIPA-1 mRNA composition or stability. In other preferred embodiments, the NIPA-1 gene sequence variation alters NIPA-1 protein sequence including amino acid substitutions, premature protein termination, and aberrant NIPA-1 mRNA splicing leading to altered NIPA-1 protein sequence.

In other embodiments, the detecting comprises detecting the NIPA-1 gene sequence variation in a nucleic acid from said sample. In further embodiments, the sample is DNA. In other embodiments, the sample is RNA.

In further embodiments, the detecting comprises detecting a polymorphic protein. In still further embodiments, the detecting a polymorphic protein occurs with an antibody. In yet other embodiments, the polymorphic protein comprises amino acid change threonine to arginine at position 45. In other embodiments, the polymporphic protein comprises additional NIPA-1 amino acid changes.

DESCRIPTION OF THE FIGURES

FIG. 6 shows the nucleic acid sequence of NIPA-1 (SEQ ID NO: 1) beginning with the start codon.

FIG. 7 shows a variant nucleic acid sequence of NIPA-1 (SEQ ID NO: 2) beginning with the start codon.

FIG. 8 shows the amino acid sequence of NIPA-1 (SEQ ID NO: 3).

FIG. 9 shows a variant amino acid sequence of NIPA-1 (SEQ ID NO: 4).

FIG. 10 shows the nucleic acid sequence of NIPA-1 (SEQ ID NO: 5).

FIG. 11 shows a variant nucleic acid sequence of NIPA-1 (SEQ ID NO: 6).

FIG. 12 shows the amino acid sequence of the wild type NIPA-1 (SEQ ID NO: 7).

FIG. 13 shows a variant amino acid sequence of the mutant NIPA-1 (SEQ ID NO: 8).

DEFINITIONS

Figure 1:
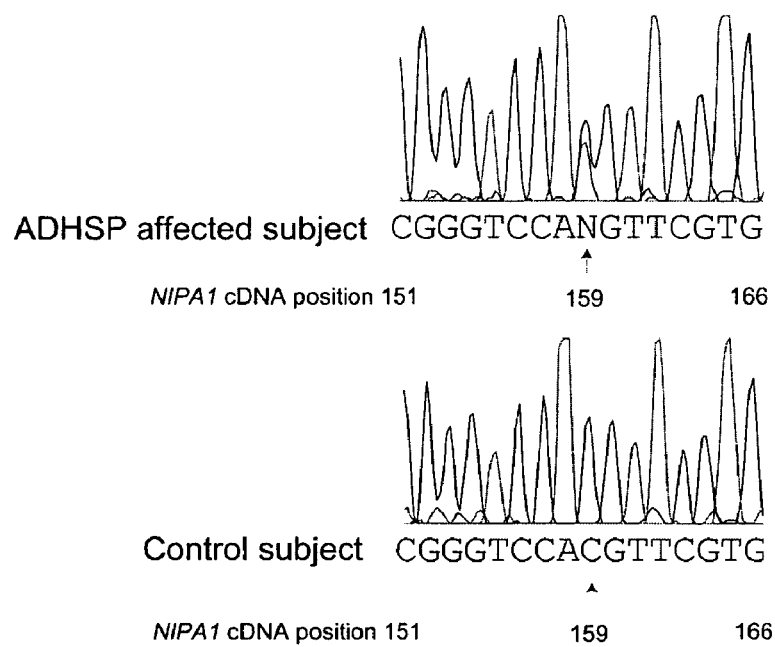
FIG. 1 shows a representative NIPA1 exon 1 sequence.

To facilitate understanding of the invention, a number of terms are defined below.

As used herein, the term "NIPA-1" when used in reference to a protein or nucleic acid refers to a NIPA-1 protein or nucleic acid encoding a NIPA-1 protein of the present invention. The term NIPA-1 encompasses both proteins that are identical to wild-type NIPA-1s and those that are derived from wild type NIPA-1 (e.g., variants of NIPA-1 polypeptides of the present invention) or chimeric genes constructed with portions of NIPA-1 coding regions). In some embodiments, the "NIPA-1" is a wild type NIPA-1 nucleic acid (SEQ ID NO: 1) or amino acid (SEQ ID NO: 3) sequence. In other embodiments, the "NIPA-1" is a variant or mutant nucleic acid (SEQ ID NO: 2) or amino acid (SEQ ID NO: 4).

As used herein, the terms "subject" and "patient" refer to any animal, such as a mammal like a dog, cat, bird, livestock, and preferably a human. Specific examples of "subjects" and "patients" include, but are not limited to, individuals with a hereditary spastic paraplegia (HSP), and individuals with HSP-related characteristics or symptoms.

As used herein, the phrase "symptoms of HSP" and "characteristics of HSP" include, but are not limited to, lower extremity weakness, bladder disturbance, impaired position sense in the legs, and neurologic deficits.

The phrase "under conditions such that the symptoms are reduced" refers to any degree of qualitative or quantitative reduction in detectable symptoms of HSP, including but not limited to, a detectable impact on the rate of recovery from disease, or the reduction of at least one symptom of HSP.

The term "siRNAs" refers to short interfering RNAs. Methods for the use of siRNAs are described in U.S. Patent App. No. 20030148519/A1 (herein incorporated by reference). In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "instructions for using said kit for said detecting the presence or absence of a variant NIPA-1 nucleic acid or polypeptide in said biological sample" includes instructions for using the reagents contained in the kit for the detection of variant and wild type NIPA-1 nucleic acids or polypeptides. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., NIPA-1). The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "NIPA-1 gene" or "NIPA-1 genes" refers to the full-length NIPA-1 nucleotide sequence (e.g., contained in SEQ ID NOs: 1 and 2). However, it is also intended that the term encompass fragments of the NIPA-1 sequences, mutants of the NIPA-1 sequences, as well as other domains within the full-length NIPA-1 nucleotide sequences. Furthermore, the terms "NIPA-1 nucleotide sequence" or "NIPA-1 polynucleotide sequence" encompasses DNA sequences, cDNA sequences, RNA (e.g., mRNA) sequences, and associated regulatory sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence 5'-"A-G-T-3'," is complementary to the sequence 3'-"T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Complementarity can include the formation of base pairs between any type of nucleotides, including non-natural bases, modified bases, synthetic bases and the like.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed.

The present invention is not limited to the hybridization of probes of about 500 nucleotides in length. The present invention contemplates the use of probes between approximately 10 nucleotides up to several thousand (e.g., at least 5000) nucleotides in length. One skilled in the relevant understands that stringency conditions may be altered for probes of other sizes (See e.g., Anderson and Young, Quantitative Filter Hybridization, in *Nucleic Acid Hybridization* [1985] and Sambrook et al., Molecular Cloning: A Laboratory Manual, Cold Spring Harbor Press, NY [1989]).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (*U.S.A.*) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., NIPA-1).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., a NIPA-1 gene of the present invention).

As used herein, the term "detection assay" refers to an assay for detecting the presence or absence of variant nucleic acid sequences (e.g., polymorphisms or mutations) in a given allele of a particular gene (e.g., a NIPA-1 gene). Examples of suitable detection assays include, but are not limited to, those described below in Section III B.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4: 560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method. Particular examples of primers useful in the present invention include, but are not limited to, a primer of least 5 nucleotides from SEQ ID NOs: 1 or 2, a primer of at least 10 nucleotides from SEQ ID NOs: 1 or 2, a primer of at least 20 nucleotides from SEQ ID NOs: 1 or 2, a primer of at least 30 nucleotides in length from SEQ ID NOs: 1 or 2, a primer of at least 40 nucleotides in length from SEQ ID NOs: 1 or 2, a primer of at least 55 nucleotides in length from SEQ ID NOs: 1 or 2, and a primer of at least 50 nucleotides in length from SEQ ID NOs: 1 or 2.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands.

The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding NIPA-1 includes, by way of example, such nucleic acid in cells ordinarily expressing NIPA-1 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" or "to purify" refers to the removal of contaminants from a sample. For example, NIPA-1 antibodies are purified by removal of contaminating non-immunoglobulin proteins; they are also purified by the removal of immunoglobulin that does not bind a NIPA-1 polypeptide. The removal of non-immunoglobulin proteins and/or the removal of immunoglobulins that do not bind a NIPA-1 polypeptide results in an increase in the percent of NIPA-1-reactive immunoglobulins in the sample. In another example, recombinant NIPA-1 polypeptides are expressed in bacterial host cells and the polypeptides are purified by the removal of host cell proteins; the percent of recombinant NIPA-1 polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein, is used to indicate a protein that does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis). Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of mRNA present in the band corresponding in size to the correctly spliced NIPA-1 transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding NIPA-1s (e.g., SEQ ID NOs:1 and 2) or fragments thereof may be employed as hybridization probes. In this case, the NIPA-1 encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "computer implemented method" refers to a method utilizing a "CPU" and "computer readable medium."

DETAILED DESCRIPTION OF THE INVENTION

The present invention relates to the NIPA-1 proteins and nucleic acids encoding the NIPA-1 proteins. The present invention further provides assays for the detection of therapeutic agents, and for the detection of NIPA-1 polymorphisms and mutations associated with disease states. Exemplary embodiments of the present invention are described below.

I. NIPA-1 Polynucleotides

As described above, the present invention provides novel NIPA-1 family genes. Accordingly, the present invention provides nucleic acids encoding NIPA-1 genes, homologs, variants (e.g., polymorphisms and mutants), including but not limited to, those described in SEQ ID NOs: 1 and 2. Table 1 describes exemplary NIPA-1 genes of the present invention. In some embodiments, the present invention provides polynucleotide sequences that are capable of hybridizing to SEQ ID NOs: 1 and 2 under conditions of low to high stringency as long as the polynucleotide sequence capable of hybridizing encodes a protein that retains a biological activity of the naturally occurring NIPA-1s. In some embodiments, the protein that retains a biological activity of naturally occurring NIPA-1 is 70% homologous to wild-type NIPA-1, preferably 80% homologous to wild-type NIPA-1, more preferably 90% homologous to wild-type NIPA-1, and most preferably 95% homologous to wild-type NIPA-1. In preferred embodiments, hybridization conditions are based on the melting temperature ($T_m$) of the nucleic acid binding complex and confer a defined "stringency" as explained above (See e.g., Wahl, et al., Meth. Enzymol., 152:399-407 [1987], incorporated herein by reference).

In other embodiments of the present invention, additional alleles of NIPA-1 genes are provided. In preferred embodiments, alleles result from a polymorphism or mutation (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence. Examples of the alleles of the present invention include that encoded by SEQ ID NO: 1 (wild type) and disease alleles thereof (e.g., SEQ ID NO: 2). Additional examples include truncation mutations (e.g., such that the encoded mRNA does not produce a complete protein).

In still other embodiments of the present invention, the nucleotide sequences of the present invention may be engineered in order to alter an NIPA-1 coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of NIPA-1 may be extended utilizing the nucleotide sequence in various methods known in the art to detect upstream sequences such as promoters and regulatory elements. For example, it is contemplated that restriction-site polymerase chain reaction (PCR) will find use in the present invention. This is a direct method that uses universal primers to retrieve unknown sequence adjacent to a known locus (Gobinda et al., PCR Methods Applic., 2:318-22 [1993]). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 [1988]). The primers may be designed using Oligo 4.0 (National Biosciences Inc, Plymouth Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055-60 [1991]). The PROMOTER-FINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present invention, variants of the disclosed NIPA-1 sequences are provided. In preferred embodiments, variants result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., NIPA-1 function) for such purposes as altering the biological activity (e.g., altered NIPA-1 function). Such modified peptides are considered functional equivalents of peptides having an activity of a NIPA-1 peptide as defined herein. A modified peptide can be produced in which the nucleotide sequence encoding the polypeptide has been altered, such as by substitution, deletion, or addition. In particularly preferred embodiments, these modifications do not significantly reduce the biological activity of the modified NIPA-1 genes. In other words, construct "X" can be evaluated in order to determine whether it is a member of the genus of modified or variant NIPA-1's of the present invention as defined functionally, rather than structurally. In preferred embodiments, the activity of variant NIPA-1 polypeptides is evaluated by methods described herein (e.g., the generation of transgenic animals or the use of signaling assays).

Moreover, as described above, variant forms of NIPA-1 genes are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of NIPA-1 disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a NIPA-1 coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

TABLE 1

NIPA-1 Genes

| NIPA-1 Gene | SEQ ID NO (Nucleic acid) | SEQ ID NO (Polypeptide) |
|---|---|---|
| NIPA-1 | 1 | 3 |
| NIPA-1*159 | 2 | 4 |

II. NIPA-1 Polypeptides

In other embodiments, the present invention provides NIPA-1 polynucleotide sequences that encode NIPA-1 polypeptide sequences (e.g., the polypeptides of SEQ ID NOs: 3 and 4). Other embodiments of the present invention provide fragments, fusion proteins or functional equivalents of these NIPA-1 proteins. In some embodiments, the present invention provides mutants of NIPA-1 polypeptides. In still other embodiments of the present invention, nucleic acid sequences corresponding to NIPA-1 variants, homologs, and mutants may be used to generate recombinant DNA molecules that direct the expression of the NIPA-1 variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NOs:1 and 2 that encode substantially the same or a functionally equivalent amino acid sequence, may be used to clone and express NIPA-1. In general, such polynucleotide sequences hybridize to SEQ ID NOs:1 and 2 under conditions of high to medium stringency as described above. As will be understood by those of skill in the art, it may be advantageous to produce NIPA-1-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) are selected, for example, to increase the rate of NIPA-1 expression or to produce recombinant RNA transcripts having desirable properties, such as a longer half-life, than transcripts produced from naturally occurring sequence.

1. Vectors for Production of NIPA-1

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOs: 1 and 2). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NOs: 1 and 2) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the E. coli lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of genes in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in E. coli).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of NIPA-1 Polypeptides

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, Escherichia coli, Salmonella typhimurium, Bacillus subtilis, and various species within the genera Pseudomonas, Streptomyces, and Staphylococcus, as well as Saccharomycees cerivisiae, Schizosaccharomycees pombe, Drosophila S2 cells, Spodoptera Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., [1989].

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

3. Purification of NIPA-1 Polypeptides

The present invention also provides methods for recovering and purifying NIPA-1 polypeptides from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having a coding sequence of a NIPA-1 gene (e.g., SEQ ID NOs: 1 and 2) fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 [1984]).

4. Truncation Mutants of NIPA-1 Polypeptide

In addition, the present invention provides fragments of NIPA-1 polypeptides (i.e., truncation mutants). In some embodiments of the present invention, when expression of a portion of the NIPA-1 protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751 [1987]) and *Salmonella typhimurium* and its in vitro activity has been demonstrated on recombinant proteins (Miller et al., Proc. Natl. Acad. Sci. USA 84:2718 [1990]). Therefore, removal of an N-terminal methionine, if desired, can be achieved either in vivo by expressing such recombinant polypeptides in a host which produces MAP (e.g., *E. coli* or CM89 or *S. cerivisiae*), or in vitro by use of purified MAP.

5. Fusion Proteins Containing NIPA-1

The present invention also provides fusion proteins incorporating all or part of the NIPA-1 polypeptides of the present invention. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a NIPA-1 protein. In some embodiments of the present invention, the VP6 capsid protein of rotavirus is used as an immunologic carrier protein for portions of a NIPA-1 polypeptide, either in the monomeric form or in the form of a viral particle. In other embodiments of the present invention, the nucleic acid sequences corresponding to the portion of a NIPA-1 polypeptide against which antibodies are to be raised can be incorporated into a fusion gene construct which includes coding sequences for a late vaccinia virus structural protein to produce a set of recombinant viruses expressing fusion proteins comprising a portion of NIPA-1 as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of a NIPA-1 polypeptide and the poliovirus capsid protein are created to enhance immunogenicity of the set of polypeptide antigens (See e.g., EP Publication No. 025949; and Evans et al., Nature 339:385 [1989]; Huang et al., J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of NIPA-1 is obtained directly from organo-chemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the NIPA-1 proteins can also be expressed and presented by bacterial cells.

In addition to utilizing fusion proteins to enhance immunogenicity, it is widely appreciated that fusion proteins can also facilitate the expression of proteins, such as a NIPA-1 protein of the present invention. Accordingly, in some embodiments of the present invention, NIPA-1 polypeptides can be generated as glutathione-S-transferase (i.e., GST fusion proteins). It is contemplated that such GST fusion proteins will enable easy purification of NIPA-1 polypeptides, such as by the use of glutathione-derivatized matrices (See e.g., Ausabel et al. (eds.), Current Protocols in Molecular Biology, John Wiley & Sons, NY [1991]). In another embodiment of the present invention, a fusion gene coding for a purification leader sequence, such as a poly-(His)/enterokinase cleavage site sequence at the N-terminus of the desired portion of a NIPA-1 polypeptide, can allow purification of the expressed NIPA-1 fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 [1987]; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of NIPA-1

Still other embodiments of the present invention provide mutant or variant forms of NIPA-1 polypeptides (i.e., muteins). It is possible to modify the structure of a peptide having an activity of a NIPA-1 polypeptide of the present invention for such purposes as enhancing therapeutic or prophylactic efficacy, disabling the protein, or stability (e.g., ex vivo shelf life, and/or resistance to proteolytic degradation in vivo). Such modified peptides are considered functional equivalents of peptides having an activity of the subject NIPA-1 proteins as defined herein. A modified peptide can be produced in which the amino acid sequence has been altered, such as by amino acid substitution, deletion, or addition.

Moreover, as described above, variant forms (e.g., mutants or polymorphic sequences) of the subject NIPA-1 proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present NIPA-1 proteins, as well as truncation mutants, and is especially useful for identifying potential variant sequences (i.e., mutants or polymorphic sequences) that are involved in neurological disorders (e.g., HSP) or resistance to neurological disorders. The purpose of screening such combinatorial libraries is to generate, for example, novel NIPA-1 variants that can act as either agonists or antagonists, or alternatively, possess novel activities all together.

Therefore, in some embodiments of the present invention, NIPA-1 variants are engineered by the present method to provide altered (e.g., increased or decreased) biological activity. In other embodiments of the present invention, combinatorially-derived variants are generated which have a selective potency relative to a naturally occurring NIPA-1. Such proteins, when expressed from recombinant DNA constructs, can be used in gene therapy protocols.

Still other embodiments of the present invention provide NIPA-1 variants that have intracellular half-lives dramatically different than the corresponding wild-type protein. For example, the altered protein can be rendered either more stable or less stable to proteolytic degradation or other cellular process that result in destruction of, or otherwise inactivate NIPA-1 polypeptides. Such variants, and the genes which encode them, can be utilized to alter the location of NIPA-1 expression by modulating the half-life of the protein. For instance, a short half-life can give rise to more transient NIPA-1 biological effects and, when part of an inducible expression system, can allow tighter control of NIPA-1 levels within the cell. As above, such proteins, and particularly their recombinant nucleic acid constructs, can be used in gene therapy protocols.

In still other embodiments of the present invention, NIPA-1 variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of NIPA-1 homologs, variants or other related proteins are aligned, preferably to promote the highest homology possible. Such a population of variants can include, for example, NIPA-1 homologs from one or more species, or NIPA-1 variants from the same species but which differ due to mutation or polymorphisms. Amino acids that appear at each position of the aligned sequences are selected to create a degenerate set of combinatorial sequences.

In a preferred embodiment of the present invention, the combinatorial NIPA-1 library is produced by way of a degenerate library of genes encoding a library of polypeptides which each include at least a portion of potential NIPA-1 protein sequences. For example, a mixture of synthetic oligonucleotides can be enzymatically ligated into gene sequences such that the degenerate set of potential NIPA-1 sequences are expressible as individual polypeptides, or alternatively, as a set of larger fusion proteins (e.g., for phage display) containing the set of NIPA-1 sequences therein.

There are many ways by which the library of potential NIPA-1 homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential NIPA-1 sequences. The synthesis of degenerate oligonucleotides is well known in the art (See e.g., Narang, Tetrahedron Lett., 39:39 [1983]; Itakura et al., Recombinant DNA, in Walton (ed.), *Proceedings of the 3rd Cleveland Symposium on Macromolecules*, Elsevier, Amsterdam, pp 273-289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386 [1980]; Roberts et al., Proc. Natl. Acad. Sci. USA 89:2429 [1992]; Devlin et al., Science 249: 404 [1990]; Cwirla et al., Proc. Natl. Acad. Sci. USA 87: 6378 [1990]; each of which is herein incorporated by reference; as well as U.S. Pat. Nos. 5,223,409, 5,198,346, and 5,096,815; each of which is incorporated herein by reference).

It is contemplated that the NIPA-1 nucleic acids of the present invention (e.g., SEQ ID NOs:1 and 2, and fragments and variants thereof) can be utilized as starting nucleic acids for directed evolution. These techniques can be utilized to develop NIPA-1 variants having desirable properties such as increased or decreased biological activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 [1996]; Leung et al., Technique, 1:11 [1989]; Eckert and Kunkel, PCR Methods Appl., 1:17-24 [1991]; Caldwell and Joyce, PCR Methods Appl., 2:28 [1992]; and Zhao and Arnold, Nuc. Acids. Res., 25:1307 [1997]). After mutagenesis, the resulting clones are selected for desirable activity (e.g., screened for NIPA-1 activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370: 324 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398 [1994]; Stemmer, Proc. Natl. Acad. Sci. USA, 91:10747 [1994]; Crameri et al., Nat. Biotech., 14:315 [1996]; Zhang et al., Proc. Natl. Acad. Sci. USA, 94:4504 [1997]; and Crameri et al., Nat. Biotech., 15:436 [1997]). Variants produced by directed evolution can be screened for NIPA-1 activity by the methods described herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of NIPA-1 homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of NIPA-1 Polypeptides

In an alternate embodiment of the invention, the coding sequence of NIPA-1 is synthesized, whole or in part, using chemical methods well known in the art (See e.g., Caruthers et al., Nucl. Acids Res. Symp. Ser., 7:215 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807 [1981]). In other embodiments of the present invention, the protein itself is produced using chemical methods to synthesize either an entire NIPA-1 amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 [1995]) and automated synthesis may be achieved, for example, using ABI 431A Peptide Synthesizer (Perkin Elmer) in accordance with the instructions provided by the manufacturer. Additionally, the amino acid sequence of a NIPA-1 polypeptide, or any part thereof, may be altered during direct synthesis and/or combined using chemical methods with other sequences to produce a variant polypeptide.

III. Detection of NIPA-1 Alleles

In some embodiments, the present invention provides methods of detecting the presence of wild type or variant (e.g., mutant or polymorphic) NIPA-1 nucleic acids or polypeptides. The detection of mutant NIPA-1 polypeptides finds use in the diagnosis of disease (e.g., inflammatory disease).

A. Detection of Variant NIPA-1 Alleles

In some embodiments, the present invention provides alleles of NIPA-1 that increase a patient's susceptibility to neurological disorders (e.g., hereditary spastic paraplegias). Any mutation that results in an altered phenotype (e.g., increase in spastic paraplegia disease or resistance to spastic paraplegia disease) is within the scope of the present invention.

Accordingly, the present invention provides methods for determining whether a patient has an increased susceptibility to a neurological disorders (e.g., ADHSP) by determining, directly or indirectly, whether the individual has a variant NIPA-1 allele. In other embodiments, the present invention provides methods for providing a prognosis of increased risk for spastic paraplegia disease to an individual based on the presence or absence of one or more variant alleles of NIPA-1.

A number of methods are available for analysis of variant (e.g., mutant or polymorphic) nucleic acid or polypeptide sequences. Assays for detection variants (e.g., polymorphisms or mutations) via nucleic acid analysis fall into several categories including, but not limited to, direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following exemplary assays are useful in the present invention: directs sequencing assays, PCR assays, mutational analysis by dHPLC (e.g., available from Transgenomic, Omaha, NE or Varian, Palo Alto, Calif.), fragment length polymorphism assays (e.g., RFLP or CFLP (See e.g. U.S. Pat. Nos. 5,843, 654; 5,843,669; 5,719,208; and 5,888,780; each of which is herein incorporated by reference)), hybridization assays (e.g., direct detection of hybridization, detection of hybridization using DNA chip assays (See e.g., U.S. Pat. Nos. 6,045,996; 5,925,525; 5,858,659; 6,017,696; 6,068,818; 6,051,380; 6,001,311; 5,985,551; 5,474,796; PCT Publications WO 99/67641 and WO 00/39587, each of which is herein incorporated by reference), enzymatic detection of hybridization (See e.g., U.S. Pat. Nos. 5,846,717, 6,090,543; 6,001,567; 5,985,557; 5,994,069; 5,962,233; 5,538,848; 5,952,174 and 5,919,626, each of which is herein incorporated by reference)), polymorphisms detected directly or indirectly (e.g., detecting sequences (other polymorphisms) that are in linkage disequilibrium with the polymorphism to be indentified; for example, other sequences in the SPG-6 locus may be used; this method is described in U.S. Pat. No. 5,612,179 (herein incorporated by reference)) and mass spectrometry assays.

In addition, assays for the detection of variant NIPA-1 proteins find use in the present invention (e.g., cell free translation methods, See e.g., U.S. Pat. No. 6,303,337, herein incorporated by reference) and antibody binding assays. The generation of antibodies that specifically recognize mutant versus wild type proteins are discussed below.

B. Kits for Analyzing Risk of Neurological Disorders

The present invention also provides kits for determining whether an individual contains a wild-type or variant (e.g., mutant or polymorphic) allele or polypeptide of NIPA-1. In some embodiments, the kits are useful determining whether the subject is at risk of developing a neurological disorder (e.g., HSP). The diagnostic kits are produced in a variety of ways. In some embodiments, the kits contain at least one reagent for specifically detecting a mutant NIPA-1 allele or protein. In preferred embodiments, the reagent is a nucleic acid that hybridizes to nucleic acids containing the mutation and that does not bind to nucleic acids that do not contain the mutation. In other embodiments, the reagents are primers for amplifying the region of DNA containing the mutation. In still other embodiments, the reagents are antibodies that preferentially bind either the wild-type or mutant NIPA-1 proteins.

In some embodiments, the kit contains instructions for determining whether the subject is at risk for a neurological disorder (e.g, ADHSP). In preferred embodiments, the instructions specify that risk for developing a spastic paraplegia disease is determined by detecting the presence or absence of a mutant NIPA-1 allele in the subject, wherein subjects having an mutant allele are at greater risk for developing a spastic paraplegia disease.

The presence or absence of a disease-associated mutation in a NIPA-1 gene can be used to make therapeutic or other medical decisions. For example, couples with a family history of spastic paraplegia diseases may choose to conceive a child via in vitro fertilization and pre-implantation genetic screening. In this case, fertilized embryos are screened for mutant (e.g., disease associated) alleles of a NIPA-1 gene and only embryos with wild type alleles are implanted in the uterus.

In other embodiments, in utero screening is performed on a developing fetus (e.g., amniocentesis or chorionic villi screening). In still other embodiments, genetic screening of newborn babies or very young children is performed. The early detection of a NIPA-1 allele known to be associated with a spastic paraplegia disease allows for early intervention (e.g., genetic or pharmaceutical therapies).

In some embodiments, the kits include ancillary reagents such as buffering agents, nucleic acid stabilizing reagents, protein stabilizing reagents, and signal producing systems (e.g., florescence generating systems as Fret systems). The test kit may be packaged in any suitable manner, typically with the elements in a single container or various containers as necessary along with a sheet of instructions for carrying out the test. In some embodiments, the kits also preferably include a positive control sample.

C. Bioinformatics

In some embodiments, the present invention provides methods of determining an individual's risk of developing a neurological disorder (e.g., HSP) based on the presence of one or more variant alleles of a NIPA-1 gene. In some embodiments, the analysis of variant data is processed by a computer using information stored on a computer (e.g., in a database). For example, in some embodiments, the present invention provides a bioinformatics research system comprising a plurality of computers running a multi-platform object oriented programming language (See e.g., U.S. Pat. No. 6,125,383; herein incorporated by reference). In some embodiments, one of the computers stores genetics data (e.g., the risk of contacting a spastic paraplegia disease associated with a given polymorphism, as well as the sequences). In some embodiments, one of the computers stores application programs (e.g., for analyzing the results of detection assays). Results are then delivered to the user (e.g., via one of the computers or via the internet.

For example, in some embodiments, a computer-based analysis program is used to translate the raw data generated by the detection assay (e.g., the presence, absence, or amount of a given NIPA-1 allele or polypeptide) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant NIPA-1 genes or polypeptides), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of developing a spastic paraplegia disease) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the association of a given NIPA-1 allele with spastic paraplegia diseases.

IV. Generation of NIPA-1 Antibodies

The present invention provides isolated antibodies or antibody fragments (e.g., FAB fragments). Antibodies can be generated to allow for the detection of a NIPA-1 proteins (e.g., wild type or mutant) of the present invention. The antibodies may be prepared using various immunogens. In one embodiment, the immunogen is a human NIPA-1 peptide to generate antibodies that recognize human NIPA-1. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against a NIPA-1 polypeptide. For the production of antibody, various host animals can be immunized by injection with the peptide corresponding to the NIPA-1 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward NIPA-1, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 [1983]) or by transforming human B cells with EBV virus in vitro (Cole et al., in *Monoclonal Antibodies and Cancer Therapy*, Alan R. Liss, pp. 77-96 [1985]).

In addition, it is contemplated that techniques described for the production of single chain antibodies (U.S. Pat. No. 4,946,778; herein incorporated by reference) will find use in producing NIPA-1 specific single chain antibodies. An additional embodiment of the invention utilizes the techniques described for the construction of Fab expression libraries (Huse et al, Science 246:1275-1281 [1989]) to allow rapid and easy identification of monoclonal Fab fragments with the desired specificity for a NIPA-1 polypeptide.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immuNIPA-1iffusion assays, in situ immunoassays (e.g., using colloidal gold, enzyme or radioisotope labels), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of NIPA-1 (e.g., for Western blotting), measuring levels thereof in appropriate biological samples, etc. The antibodies can be used to detect a NIPA-1 in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of a human NIPA-1 using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of NIPA-1 detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of NIPA-1 or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of NIPA-1. Such antibodies can also be used diagnostically to measure abnormal expression of NIPA-1, or the aberrant formation of protein complexes, which may be indicative of a disease state.

V. Gene Therapy Using NIPA-1

The present invention also provides methods and compositions suitable for gene therapy to alter NIPA-1 expression, production, or function. As described above, the present invention provides human NIPA-1 genes and provides methods of obtaining NIPA-1 genes from other species. Thus, the methods described below are generally applicable across many species. In some embodiments, it is contemplated that the gene therapy is performed by providing a subject with a wild-type allele of a NIPA-1 gene (i.e., an allele that does not contain a NIPA-1 disease allele (e.g., free of disease causing polymorphisms or mutations). Subjects in need of such therapy are identified by the methods described above. In some embodiments, transient or stable therapeutic nucleic acids are used (e.g., antisense oligonucleotides, siRNAs) to reduce or prevent expression of mutant proteins.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mav1, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In a preferred embodiment, the adenoviral vector has a deletion in the E1 region (Ad 1.0). Examples of E1-deleted adenoviruses are disclosed in EP 185, 573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. Nos. 4,797,368; 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus") MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

VI. Transgenic Animals Expressing Exogenous NIPA-1 Genes and Homologs, Mutants, and Variants Thereof The present invention contemplates the generation of transgenic animals comprising an exogenous NIPA-1 gene or homologs, mutants, or variants thereof. In preferred embodiments, the transgenic animal displays an altered phenotype as compared to wild-type animals. In some embodiments, the altered phenotype is the overexpression of mRNA for a NIPA-1 gene as compared to wild-type levels of NIPA-1 expression. In other embodiments, the altered phenotype is the decreased expression of mRNA for an endogenous NIPA-1 gene as compared to wild-type levels of endogenous NIPA-1 expression. In some preferred embodiments, the transgenic animals comprise mutant alleles of NIPA-1. Methods for analyzing the presence or absence of such phenotypes include Northern blotting, mRNA protection assays, and RT-PCR. In other embodiments, the transgenic mice have a knock out mutation of a NIPA-1 gene. In preferred embodiments, the transgenic animals display an altered susceptibility to neurological disorders (e.g., HSP).

Such animals find use in research applications (e.g., identifying signaling pathways that a NIPA-1 protein is involved in), as well as drug screening applications (e.g., to screen for drugs that prevent or treat neurological disorders). For example, in some embodiments, test compounds (e.g., a drug that is suspected of being useful to treat a spastic paraplegia disease) are administered to the transgenic animals and control animals with a wild type NIPA-1 allele and the effects evaluated. The effects of the test and control compounds on disease symptoms are then assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad. Sci. USA 82:6927 [1985]). Transfection is easily and efficiently obtained by culturing the blastomeres on a monolayer of virus-producing cells (Van der Putten, supra; Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the microinjection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., mutants in which a particular domain of a NIPA-1 is deleted). Methods for homologous recombination are described in U.S. Pat. No. 5,614,396, incorporated herein by reference.

VIII. Drug Screening Using NIPA-1

In some embodiments, the isolated nucleic acid and polypeptides of NIPA-1 genes of the present invention (e.g., SEQ ID NOS: 1-4) and related proteins and nucleic acids are used in drug screening applications for compounds that alter (e.g., enhance or inhibit) NIPA-1 activity and signaling. The present invention further provides methods of identifying ligands and signaling pathways of the NIPA-1 proteins of the present invention.

The present invention is not limited to a particular mechanism. Indeed, an understanding of the mechanism is not necessary to practice the present invention. Nonetheless, based upon a hydrophobicity analysis of NIPA-1 family proteins (see Chai et al, Am J Hum Genet (2003 in press)), it is contemplated that NIPA-1 family proteins function as receptors or transporters.

In some embodiments, the present invention provides methods of screening compounds for the ability to alter NIPA-1 activity mediated by natural ligands (e.g., identified using the methods described above). Such compounds find use in the treatment of disease mediated by NIPA-1 family members (e.g., HSP).

In some embodiments, the present invention provides methods of screening compounds for an ability to interact with mutant NIPA-1 nucleic acid (e.g., SEQ ID NO: 2) and/or mutant NIPA-1 polypeptides (e.g., SEQ ID NO: 4), while simultaneously not interacting with wild type NIPA-1 nucleic acid (e.g., SEQ ID NO: 1) and/or wild type NIPA-1 polypeptides (e.g., SEQ ID NO: 3). Such compounds find use in the treatment of neurological disorders facilitated by the presence of mutant forms of NIPA-1 nucleic acids and/or proteins.

In one screening method, the two-hybrid system is used to screen for compounds (e.g., proteins) capable of altering NIPA-1 function(s) (e.g., interaction with a binding partner) in vitro or in vivo. In one embodiment, a GAL4 binding site, linked to a reporter gene such as lacZ, is contacted in the presence and absence of a candidate compound with a GAL4 binding domain linked to a NIPA-1 fragment and a GAL4 transactivation domain II linked to a binding partner fragment. Expression of the reporter gene is monitored and a decrease in the expression is an indication that the candidate compound inhibits the interaction of a NIPA-1 with the binding partner. Alternately, the effect of candidate compounds on the interaction of a NIPA-1 with other proteins (e.g., proteins known to interact directly or indirectly with the binding partner) can be tested in a similar manner.

In some embodiments, the present invention provides methods of identifying NIPA-1 binding partners or ligands that utilize immunoprecipitation. In some embodiments, antibodies to NIPA-1 proteins are utilized to immunoprecipitated NIPA-1s and any bound proteins. In other embodiments, NIPA-1 fusion proteins are generated with tags and antibodies to the tags are utilized for immunoprecipitation. Potential binding partners that immunoprecipitate with NIPA-1s can be identified using any suitable method.

In another screening method, candidate compounds are evaluated for their ability to alter NIPA-1 activity by contacting NIPA-1, binding partners, binding partner-associated proteins, or fragments thereof, with the candidate compound and determining binding of the candidate compound to the peptide. The protein or protein fragments is/are immobilized using methods known in the art such as binding a GST-NIPA-1 fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 [1988]). The fusion construct is then transformed into a suitable expression system (e.g., *E. coli* XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate NIPA-1 physiological effects (e.g., spastic paraplegia).

In another screening method, one of the components of the NIPA-1/binding partner signaling system is immobilized. Polypeptides can be immobilized using methods known in the art, such as adsorption onto a plastic microtiter plate or specific binding of a GST-fusion protein to a polymeric bead containing glutathione. For example, in some embodiments, GST-NIPA-1 is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of NIPA-1 with the other peptide. A variation of this method allows for the screening of compounds that are capable of disrupting a previously-formed protein/protein complex. For example, in some embodiments a complex comprising a NIPA-1 or a NIPA-1 fragment bound to another peptide is immobilized as described above and contacted with a candidate compound. The dissolution of the complex by the candidate compound correlates with the ability of the compound to disrupt or inhibit the interaction between NIPA-1 and the other peptide.

Another technique for drug screening provides high throughput screening for compounds having suitable binding affinity to NIPA-1 peptides and is described in detail in WO 84/03564, incorporated herein by reference. Briefly, large numbers of different small peptide test compounds are synthesized on a solid substrate, such as plastic pins or some other surface. The peptide test compounds are then reacted with NIPA-1 peptides and washed. Bound NIPA-1 peptides are then detected by methods well known in the art.

Another technique uses NIPA-1 antibodies, generated as discussed above. Such antibodies are capable of specifically binding to NIPA-1 peptides and compete with a test compound for binding to NIPA-1. In this manner, the antibodies can be used to detect the presence of any peptide that shares one or more antigenic determinants of a NIPA-1 peptide.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with NIPA-1 genes and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding NIPA-1 or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. In some embodiments, the reporter gene construct comprises the 5' regulatory region (e.g., promoters and/or enhancers) of a protein whose expression is controlled by NIPA-1 in operable association with a reporter gene. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminecent products of specific substrates (e.g., X-gal and luciferin). Comparisons between compounds of known and unknown activities may be conducted as described above.

Specifically, the present invention provides screening methods for identifying modulators, i.e., candidate or test compounds or agents (e.g., proteins, peptides, peptidomimetics, peptoids, small molecules or other drugs) which bind to a NIPA-1 of the present invention, have an inhibitory (or stimulatory) effect on, for example, NIPA-1 expression or NIPA-1 activity, or have a stimulatory or inhibitory effect on, for example, the expression or activity of a NIPA-1 substrate. Compounds thus identified can be used to modulate the activity of target gene products (e.g., NIPA-1 genes) either directly or indirectly in a therapeutic protocol, to elaborate the biological function of the target gene product, or to identify compounds that disrupt normal target gene interactions. Compounds, which stimulate the activity of a variant NIPA-1 or mimic the activity of a non-functional variant are particularly useful in the treatment of neurological disorders (e.g., HSP).

In one embodiment, the invention provides assays for screening candidate or test compounds that are substrates of a NIPA-1 protein or polypeptide or a biologically active portion thereof. In another embodiment, the invention provides assays for screening candidate or test compounds that bind to or modulate the activity of a NIPA-1 protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222: 301 [1991]).

In one embodiment, an assay is a cell-based assay in which a cell that expresses a NIPA-1 protein or biologically active portion thereof is contacted with a test compound, and the ability of the test compound to modulate a NIPA-1's activity is determined. Determining the ability of the test compound to modulate NIPA-1 activity can be accomplished by monitoring, for example, changes in enzymatic activity. The cell, for example, can be of mammalian origin.

The ability of the test compound to modulate NIPA-1 binding to a compound, e.g., a NIPA-1 substrate, can also be evaluated. This can be accomplished, for example, by coupling the compound, e.g., the substrate, with a radioisotope or enzymatic label such that binding of the compound, e.g., the substrate, to a NIPA-1 can be determined by detecting the labeled compound, e.g., substrate, in a complex.

Alternatively, a NIPA-1 is coupled with a radioisotope or enzymatic label to monitor the ability of a test compound to modulate NIPA-1 binding to a NIPA-1 substrate in a complex. For example, compounds (e.g., substrates) can be labeled with $^{125}I$, $^{35}S$ $^{14}C$ or $^3H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a NIPA-1 substrate) to interact with a NIPA-1 with or without the labeling of any of the interactants can be evaluated. For example, a microphysiometer can be used to detect the interaction of a compound with a NIPA-1 without the labeling of either the compound or the NIPA-1 (McConnell et al. Science 257: 1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and a NIPA-1 polypeptide.

In yet another embodiment, a cell-free assay is provided in which a NIPA-1 protein or biologically active portion thereof is contacted with a test compound and the ability of the test compound to bind to the NIPA-1 protein or biologically active portion thereof is evaluated. Preferred biologically active portions of NIPA-1 proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 15 the assay should be maximal. An FRET binding event can be conveniently measured through standard fluorometric detection means well known in the art (e.g., using a fluorimeter).

In another embodiment, determining the ability of a NIPA-1 protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)); resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize a NIPA-1 protein, an anti-NIPA-1 antibody or its target molecule to facilitate separation of complexed from non-complexed forms of one or both of the proteins, as well as to accommodate automation of the assay. Binding of a test compound to a NIPA-1 protein, or interaction of a NIPA-1 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-NIPA-1 fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or NIPA-1 protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of NIPA-1 binding or activity determined using standard techniques. Other techniques for immobilizing either a NIPA-1 protein or a target molecule on matrices include using conjugation of biotin and streptavidin. Biotinylated NIPA-1 protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with NIPA-1 protein or target molecules but which do not interfere with binding of the NIPA-1 protein to its target molecule. Such antibodies can be derivatized to the wells of the plate, and unbound target or NIPA-1 protein trapped in the wells by antibody conjugation. Methods for detecting such complexes, in addition to those described above for the GST-immobilized complexes, include immuNIPA-1etection of complexes using antibodies reactive with the NIPA-1 protein or target molecule, as well as enzyme-linked assays which rely on detecting an enzymatic activity associated with the NIPA-1 protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 [1998]; Hageand Tweed J. Chromatogr. Biomed. Sci. Appl 699:499-525 [1997]). Further, fluorescence energy transfer may also be conveniently utilized, as described herein, to detect binding without further purification of the complex from solution.

The assay can include contacting the NIPA-1 protein or biologically active portion thereof with a known compound that binds the NIPA-1 to form an assay mixture, contacting the assay mixture with a test compound, and determining the ability of the test compound to interact with a NIPA-1 protein, wherein determining the ability of the test compound to interact with a NIPA-1 protein includes determining the ability of the test compound to preferentially bind to NIPA-1 or biologically active portion thereof, or to modulate the activity of a target molecule, as compared to the known compound.

To the extent that a NIPA-1 can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, a NIPA-1 protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with a NIPA-1 ("NIPA-1-binding proteins" or "NIPA-1-bp") and are involved in NIPA-1 activity. Such NIPA-L-bps can be activators or inhibitors of signals by the NIPA-1 proteins or targets as, for example, downstream elements of a NIPA-1-mediated signaling pathway.

Modulators of NIPA-1 expression can also be identified. For example, a cell or cell free mixture is contacted with a candidate compound and the expression of a NIPA-1 mRNA or protein evaluated relative to the level of expression of the NIPA-1 mRNA or protein in the absence of the candidate compound. When expression of the NIPA-1 mRNA or protein is greater in the presence of the candidate compound than in its absence, the candidate compound is identified as a stimulator of a NIPA-1 mRNA or protein expression. Alternatively, when expression of NIPA-1 mRNA or protein is less (i.e., statistically significantly less) in the presence of the candidate compound than in its absence, the candidate compound is identified as an inhibitor of NIPA-1 mRNA or protein expression. The level of NIPA-1 mRNA or protein expression can be determined by methods described herein for detecting NIPA-1 mRNA or protein.

A modulating agent can be identified using a cell-based or a cell free assay, and the ability of the agent to modulate the activity of a NIPA-1 protein can be confirmed in vivo, e.g., in an animal such as an animal model for a disease (e.g., an animal with HSP).

B. Therapeutic Agents

This invention further pertains to novel agents identified by the above-described screening assays. Accordingly, it is within the scope of this invention to further use an agent identified as described herein (e.g., a NIPA-1 modulating agent or mimetic, a NIPA-1 specific antibody, or a NIPA-1-binding partner) in an appropriate animal model (such as those described herein) to determine the efficacy, toxicity, side effects, or mechanism of action, of treatment with such an agent. Furthermore, as described above, novel agents identified by the above-described screening assays can be, e.g., used for treatments of neurological disorders (e.g., including, but not limited to, HSP). In some embodiments, the agents are NIPA-1 ligands or ligand analogs (e.g., identified using the drug screening methods described above).

IX. Pharmaceutical Compositions Containing NIPA-1 Nucleic Acid, Peptides, and Analogs The present invention further provides pharmaceutical compositions which may comprise all or portions of NIPA-1 polynucleotide sequences, NIPA-1 polypeptides, inhibitors or antagonists of NIPA-1 bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by mutant NIPA-1 alleles (e.g., spastic paraplegia diseases). Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, NIPA-1 nucleotide and NIPA-1 amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, NIPA-1 polynucleotide sequences or NIPA-1 amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of NIPA-1 may be that amount that suppresses spastic paraplegia related symptoms. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of NIPA-1, conditions indicated on the label may include treatment of condition related to spastic paraplegia diseases.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts NIPA-1 levels.

A therapeutically effective dose refers to that amount of NIPA-1 that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.01 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for NIPA-1 than for the inhibitors of NIPA-1. Administration to the bone marrow may necessitate delivery in a manner different from intravenous injections.

X. RNA Interference (RNAi)

RNAi represents an evolutionary conserved cellular defense for controlling the expression of foreign genes in most eukaryotes, including humans. RNAi is triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3): 158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing Brummelkamp et al, Science 2002; 296:550-3; and Holen et al, Nucleic Acids Res. 2002; 30:1757-66, both of which are herein incorporated by reference.

XI. RNAi for NIPA-1

As discussed above, the present invention provides RNAi for inhibiting the expression of the NIPA-1 polypeptide in cells. Preferably, inhibition of the level of NIPA-1 expression in cells prevents and/or reduces the symptoms of HSP.

A. Designing and Testing RNAi for NIPA-1

In order to design siRNAs for NIPA-1 (e.g. that target NIPA-1 mRNA) software design tools are available in the art (e.g. on the internet). For example, Oligoengine's web page has one such design tool that finds RNAi candidates based on Elbashir's (Elbashir et al, Methods 2002; 26: 199-213, herein incorporated by reference) criteria. Other design tools may also be used, such as the Cenix Bioscience design tool offered by Ambion. In addition, there is also the Si2 silencing duplex offered by Oligoengine.

There are also RNA folding software programs available that allow one to determine if the mRNA has a tendency to fold on its own and form a "hair-pin" (which in the case of dsRNAi is not as desirable since one goal is to have the RNAi attach to the mRNA and not itself). One preferred configuration is an open configuration with three or less bonds. Generally, a positive delta G is desirable to show that it would not tend to fold on itself spontaneously.

siRNA candidate molecules that are generated can be, for example, screened in an animal model of HSP for the quantitative evaluation of NIPA-1 expression in vivo using similar techniques as described above.

B. Expression Cassettes

NIPA-1 specific siRNAs of the present invention may be synthesized chemically. Chemical synthesis can be achieved by any method known or discovered in the art. Alternatively, NIPA-1 specific siRNAs of the present invention may be synthesized by methods which comprise synthesis by transcription. In some embodiments, transcription is in vitro, as from a DNA template and bacteriophage RNA polymerase promoter, in other embodiments, synthesis is in vivo, as from a gene and a promoter. Separate-stranded duplex siRNA, where the two strands are synthesized separately and annealed, can also be synthesized chemically by any method known or discovered in the art. Alternatively, ds siRNA are synthesized by methods which comprise synthesis by transcription. In some embodiments, the two strands of the double-stranded region of a siRNA are expressed separately by two different expression cassettes, either in vitro (e.g., in a transcription system) or in vivo in a host cell, and then brought together to form a duplex.

Thus, in another aspect, the present invention provides a composition comprising an expression cassette comprising a promoter and a gene that encodes a siRNA specific for NIPA-1. In some embodiments, the transcribed siRNA forms a single strand of a separate-stranded duplex (or double-stranded, or ds) siRNA of about 18 to 25 base pairs long; thus, formation of ds siRNA requires transcription of each of the two different strands of a ds siRNA. The term "gene" in the expression cassette refers to a nucleic acid sequence that comprises coding sequences necessary for the production of a siRNA. Thus, a gene includes but is not limited to coding sequences for a strand of a ds siRNA.

Generally, a DNA expression cassette comprises a chemically synthesized or recombinant DNA molecule containing at least one gene, or desired coding sequence for a single strand of a ds siRNA, and appropriate nucleic acid sequences necessary for the expression of the operably linked coding sequence, either in vitro or in vivo. Expression in vitro may include expression in transcription systems and in transcription/translation systems. Expression in vivo may include expression in a particular host cell and/or organism. Nucleic acid sequences necessary for expression in a prokaryotic cell or in a prokaryotic in vitro expression system are well known and usually include a promoter, an operator, and a ribosome binding site, often along with other sequences. Eukaryotic in vitro transcription systems and cells are known to utilize promoters, enhancers, and termination and polyadenylation signals. Nucleic acid sequences necessary for expression via bacterial RNA polymerases (such as T3, T7, and SP6), referred to as a transcription template in the art, include a template DNA strand which has a polymerase promoter region followed by the complement of the RNA sequence desired (or the coding sequence or gene for the siRNA). In order to create a transcription template, a complementary strand is annealed to the promoter portion of the template strand.

In any of the expression cassettes described above, the gene may encode a transcript that contains at least one cleavage site, such that when cleaved results in at least two cleavage products. Such products can include the two opposite strands of a ds siRNA. In an expression system for expression in a eukaryotic cell, the promoter may be constitutive or inducible; the promoter may also be tissue or organ specific (e.g. specific to the eye), or specific to a developmental phase. Preferably, the promoter is positioned 5' to the transcribed region. Other promoters are also contemplated; such promoters include other polymerase III promoters and microRNA promoters.

Preferably, a eukaryotic expression cassette further comprises a transcription termination signal suitable for use with the promoter; for example, when the promoter is recognized by RNA polymerase III, the termination signal is an RNA polymerase III termination signal. The cassette may also include sites for stable integration into a host cell genome.

C. Vectors

In other aspects of the present invention, the compositions comprise a vector comprising a gene encoding an siRNA specific for NIPA-1 or preferably at least one expression cassette comprising a promoter and a gene which encodes a sequence necessary for the production of a siRNA specific for NIPA-1 (an siRNA gene). The vectors may further comprise marker genes, reporter genes, selection genes, or genes of interest, such as experimental genes. Vectors of the present invention include cloning vectors and expression vectors. Expression vectors may be used in in vitro transcription/translation systems, as well as in in vivo in a host cell. Expression vectors used in vivo in a host cell may be transfected into a host cell, either transiently, or stably. Thus, a vector may also include sites for stable integration into a host cell genome.

In some embodiments, it is useful to clone a siRNA gene downstream of a bacteriophage RNA polymerase promoter into a multicopy plasmid. A variety of transcription vectors containing bacteriophage RNA polymerase promoters (such as T7 promoters) are available. Alternatively, DNA synthesis can be used to add a bacteriophage RNA polymerase promoter upstream of a siRNA coding sequence. The cloned plasmid DNA, linearized with a restriction enzyme, can then be used as a transcription template (See for example Milligan, J F and Uhlenbeck, O C (1989) Methods in Enzymology 180: 51-64).

In other embodiments of the present invention, vectors include, but are not limited to, chromosomal, nonchromosomal and synthetic DNA sequences (e.g., derivatives of viral DNA such as vaccinia, adenovirus, fowl pox virus, and pseudorabies). It is contemplated that any vector may be used as long as it is expressed in the appropriate system (either in vitro or in vivo) and viable in the host when used in vivo; these two criteria are sufficient for transient transfection. For stable transfection, the vector is also replicable in the host.

Large numbers of suitable vectors are known to those of skill in the art, and are commercially available. In some embodiments of the present invention, mammalian expression vectors comprise an origin of replication, suitable promoters and enhancers, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, a gene sequence in an expression vector which is not part of an expression cassette comprising a siRNA gene (specific for NIPA-1) is operatively linked to an appropriate expression control sequence(s) (promoter) to direct mRNA synthesis. In some embodiments, the gene sequence is a marker gene or a selection gene. Promoters useful in the present invention include, but are not limited to, the cytomegalovirus (CMV) immediate early, herpes simplex virus (HSV) thymidine kinase, and mouse metallothionein promoters and other promoters known to control expression of gene in mammalian cells or their viruses. In other embodiments of the present invention, recombinant expression vectors include origins of replication and selectable markers permitting transformation of the host cell (e.g., dihydrofolate reductase or neomycin resistance for eukaryotic cell culture).

In some embodiments of the present invention, transcription of DNA encoding a gene is increased by inserting an enhancer sequence into the vector. Enhancers are cis-acting elements of DNA, usually about from 10 to 300 bp that act on a promoter to increase its transcription. Enhancers useful in the present invention include, but are not limited to, a cytomegalovirus early promoter enhancer, the polyoma enhancer on the late side of the replication origin, and adenovirus enhancers.

Preferably the design of a vector is configured to deliver the RNAi for more permanent inhibition. For example the pSilencer siRNA expression vector offered by Ambion, the pSuper RNAi system offered by Oligoengine, and the Gne-Silencer System offered by IMGENEX. These are all plasmid vector based RNAis. BD Biosciences offer the RNAi-Ready pSIREN Vectors, that allow both a Plasmid-based vectors and an Adenoviral or a Retroviral delivery formats. Ambion is expected to release an adenoviral vector for siRNA shortly. For the design of a vector there is no limitation regarding the folding pattern since there is no concern regarding the formation of a hairpin or at least there are no studies that found any difference in performance related to the mRNA folding pattern. Therefore, SEQ ID NOS: 1 and 2, for example, may be used with in a Vector (both Plasmid and Viral) delivery systems.

It is noted that Ambion offers a design tool for a vector on their web page, and BD Biosciences offers a manual for the design of a vector, both of which are useful for designing vectors for siRNA.

D. Transfecting Cells

In yet other aspects, the present invention provides compositions comprising cells transfected by an expression cassette of the present invention as described above, or by a vector of the present invention, where the vector comprises an expression cassette (or simply the siRNA gene) of the present invention, as described above. In some embodiments of the present invention, the host cell is a mammalian cell. A transfected cell may be a cultured cell or a tissue, organ, or organismal cell. Specific examples of cultured host cells include, but are not limited to, Chinese hamster ovary (CHO) cells, COS-7 lines of monkey kidney fibroblasts, 293T, C127, 3T3, HeLa, and BHK cell lines. Specific examples of host cells in vivo include tumor tissue and eye tissue.

The cells may be transfected transiently or stably (e.g. DNA expressing the siRNA is stably integrated and expressed by the host cell's genome). The cells may also be transfected with an expression cassette of the present invention, or they are transfected with an expression vector of the present invention. In some embodiments, transfected cells are cultured mammalian cells, preferably human cells. In other embodiments, they are tissue, organ, or organismal cells.

In the present invention, cells to be transfected in vitro are typically cultured prior to transfection according to methods which are well known in the art, as for example by the preferred methods as defined by the American Tissue Culture Collection. In certain embodiments of the present invention, cells are transfected with siRNAs that are synthesized exogenously (or in vitro, as by chemical methods or in vitro transcription methods), or they are transfected with expression cassettes or vectors, which express siRNAs within the transfected cell.

In some embodiments, cells are transfected with siRNAs by any method known or discovered in the art which allows a cell to take up exogenous RNA and remain viable. Non-limiting examples include electroporation, microinjection, transduction, cell fusion, DEAE dextran, calcium phosphate precipitation, use of a gene gun, osmotic shock, temperature shock, and electroporation, and pressure treatment. In alternative, embodiments, the siRNAs are introduced in vivo by lipofection, as has been reported (as, for example, by Elbashir et al. (2001) Nature 411: 494-498, herein incorporated by reference).

In other embodiments expression cassettes or vectors comprising at least one expression cassette are introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al. (1992) J. Biol. Chem., 267:963; Wu and Wu (1988) J. Biol. Chem., 263: 14621; and Williams et al. (1991) Proc. Natl. Acad. Sci. USA 88:272). Receptor-mediated DNA delivery approaches are also used (Curiel et al. (1992) Hum. Gene Ther., 3:147; and Wu and Wu (1987) J. Biol. Chem., 262:4429). In some embodiments, various methods are used to enhance transfection of the cells. These methods include but are not limited to osmotic shock, temperature shock, and electroporation, and pressure treatment.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker. The use of cationic lipids may promote encapsulation of negatively charged nucleic acids, and also promote fusion with negatively charged cell membranes. Particularly useful lipid compounds and compositions for transfer of nucleic acids are described in WO95/18863 and WO96/17823, and in U.S. Pat. No. 5,459,127, herein incorporated by reference. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a sequence encoding a siRNA in vivo as a naked DNA, either as an expression cassette or as a vector. Methods for formulating and administering naked DNA to mammalian muscle tissue are disclosed in U.S. Pat. Nos. 5,580,859 and 5,589,466, both of which are herein incorporated by reference.

Stable transfection typically requires the presence of a selectable marker in the vector used for transfection. Transfected cells are then subjected to a selection procedure. Generally, selection involves growing the cells in a toxic substance, such as G418 or Hygromycin B, such that only those cells expressing a transfected marker gene conferring resistance to the toxic substance upon the transfected cell survive and grow. Such selection techniques are well known in the art. Typical selectable markers are well known, and include genes encoding resistance to G418 or hygromycin B.

In preferred embodiments, the transfecting agent is OLIGOFECTAMINE. OLIGOFECTAMINE is a lipid based transfection reagent. Additional example of lipid based transfection reagents that were designed for the transfection of dsRNAis are the Transit-TKO reagent which is provided by Mirus (Madison, Wis.) and the jetSI which was introduced by Polyplus-trasfection SAS. In addition, the Silencer siRNA Transfection Kit provided by Ambion's includes siPORT Amine and siPORT Lipid transfection agents. Roche offers the Fugene 6 transfection reagents that are also lipid based. There is an option to use electroporation in cell culture. Preferably a plasmid vector delivery system is transfected into the cell with OLIGOFECTAMINE provided by Invitrogen or with siPORT XP-1 transfection agent provided by Ambion.

In certain embodiments, certain chemical modifications of the dsRNAis such as changing the lipophilicity of the molecule may be employed (e.g., attachment of lipophilic residues at the 3' termini of the dsRNA). Delivery of dsRNAs into organisms may also be achieved with methods previously developed for the application of antisense oligonucleotides such as injection of liposomes-encapsulated molecules.

E. Kits

The present invention also provides kits comprising at least one expression cassette comprising a siRNA gene specific for NIPA-1. In some aspects, a transcript from the expression cassette forms a double stranded siRNA of about 18 to 25 base pairs long. In other embodiments, the expression cassette is contained within a vector, as described above, where the vector can be used in in vitro transcription or transcription/translation systems, or used in vivo to transfect cells, either transiently or stably.

In other aspects, the kit comprises at least two expression cassettes, each of which comprises a siRNA gene, such that at least one gene-encodes one strand of a siRNA that combines with a strand encoded by a second cassette to form a ds siRNA; the ds siRNA so produced is any of the embodiments described above. These cassettes may comprise a promoter and a sequence encoding one strand of a ds siRNA. In some further embodiments, the two expression cassettes are present in a single vector; in other embodiments, the two expression cassettes are present in two different vectors. A vector with at least one expression cassette, or two different vectors, each comprising a single expression cassette, can be used in in vitro transcription or transcription/translation systems, or used in vivo to transfect cells, either transiently or stably.

In yet other aspects, the kit comprises at least one expression cassettes which comprises a gene which encodes two separate strands of a ds siRNA and a processing site between the sequences encoding each strand such that, when the gene is transcribed, the transcript is processed, such as by cleavage, to result in two separate strands which can combine to form a ds siRNA, as described above.

In some embodiments, the present invention provides kits comprising; a) a composition comprising small interfering RNA duplexes (siRNAs) configured to inhibit expression of the NIPA-1 protein, and b) printed material with instructions for employing the composition for treating a target cell expressing NIPA-1 protein via expression of NIPA-1 mRNA under conditions such that the NIPA-1 mRNA is cleaved or otherwise disabled. In certain embodiments, the printed material comprises instructions for employing the composition for treating eye disease.

F. Generating NIPA-1 Specific siRNA

The present invention also provides methods of synthesizing siRNAs specific for NIPA-1 (e.g. human NIPA-1) or specific for mutant or wild type forms of NIPA-1. The siRNAs may be synthesized in vitro or in vivo. In vitro synthesis includes chemical synthesis and synthesis by in vitro transcription. In vitro transcription is achieved in a transcription system, as from a bacteriophage RNA polymerase, or in a transcription/translation system, as from a eukaryotic RNA polymerase. In vivo synthesis occurs in a transfected host cell.

The siRNAs synthesized in vitro, either chemically or by transcription, are used to transfect cells. Therefore, the present invention also provides methods of transfecting host cells with siRNAs synthesized in vitro; in particular embodiments, the siRNAs are synthesized by in vitro transcription. The present invention further provides methods of silencing the NIPA-1 gene in vivo by transfecting cells with siRNAs synthesized in vitro. In other methods, the siRNAs is expressed in vitro in a transcription/translation system from an expression cassette or expression vector, along with an expression vector encoding and expressing a reporter gene.

The present invention also provides methods of expressing siRNAs in vivo by transfecting cells with expression cassettes or vectors which direct synthesis of siRNAs in vivo. The present invention also provides methods of silencing genes in vivo by transfecting cells with expression cassettes or vectors that direct synthesis of siRNAs in vivo.

EXAMPLES

The following examples are provided in order to demonstrate and further illustrate certain preferred embodiments and aspects of the present invention and are not to be construed as limiting the scope thereof.

ADHSP does not Result from Genetic Imprinting in Chromosome 15q11-13 (SPG-6 Locus)

Ten ADHSP loci have been mapped, and four ADHSP genes have been identified—SPG4/spastin, SPG3A/atlastin, SPG13/chaperonin 60 and SPG10/KIF5A (Hazan et al, Nat Genet 23:296-303 (1999); Zhao et al, Nat Genet 29:326-331 (2001); Hansen et al, Am J Hum Genet 70:1328-1332 (2002); Reid et al, Am J Hum Genet 71:1189-1194 (2002)). Despite these advances, the molecular pathophysiology of the ADHSPs is unknown. A locus for uncomplicated ADHSP is located in chromosome 15q (SPG6) (Fink et al, Am J Hum Genet 56:188-92 (1995); Fink et al, Neurology 45:325-31 (1995)).

Figure 2:
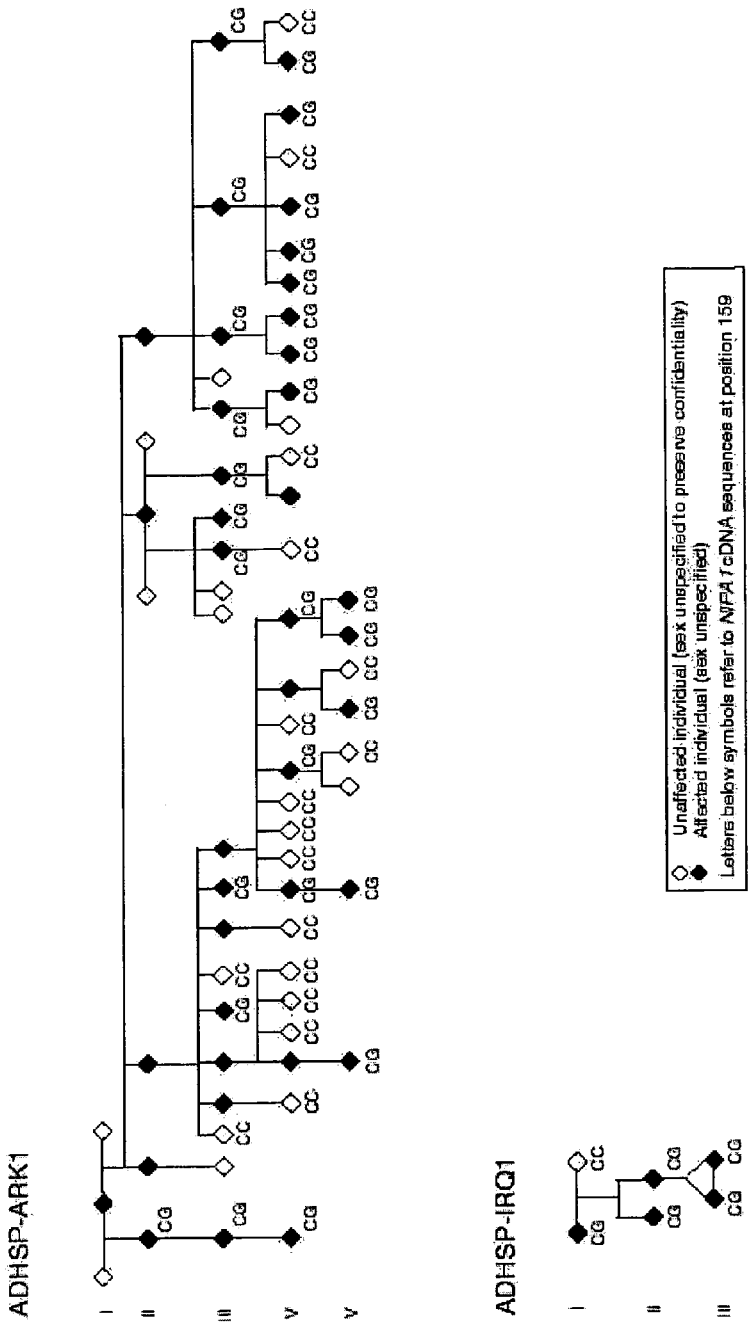
FIG. 2 shows ADHSP kindreds showing NIPA1 sequence at cDNA position 159.
Figure 3:
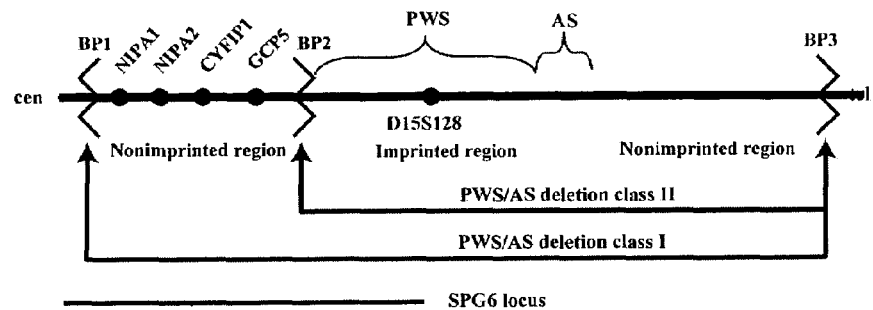
FIG. 3 shows SPG6 occurs in regions deleted in Prader-Willi (PWS) and Angleman syndromes (AS).
Figure 4:
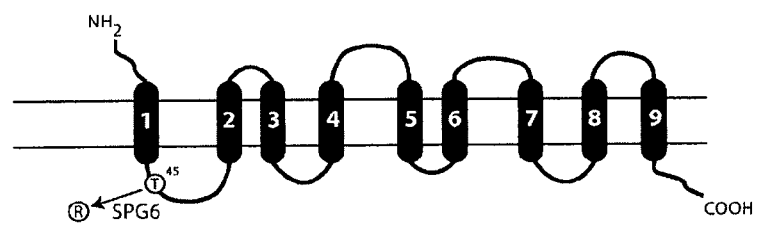
FIG. 4 shows the NIPA1 secondary structure.
Figure 5:
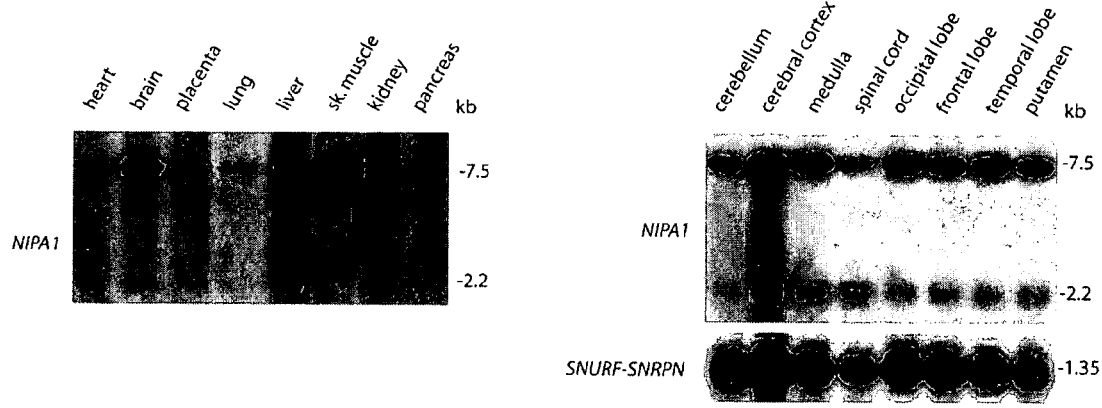
FIG. 5 shows expression of NIPA1 by Northern Blot analysis.

The SPG6 locus extends 6.1 cM between D15S128 and the centromere (Rainier et al, Am J Hum Genet 67:91 (2000) (FIG. 2a). This interval is involved in deletions that result in Prader-Willi syndrome (PWS) or Angelman syndrome (AS). PWS and AS are characterized by genetic imprinting (Nicholls and Knepper, Ann Rev Genomics Hum Genet 2:153-175 (2001)). Studies conducted in the course of the present invention involved analysis of a large kindred, ADHSP-ARK1 (FIG. 1b), in which ADHSP was linked to the SPG6 locus. Analysis of the ADHSP-ARK1 kindred indicated no evidence of genetic imprinting (Fink et al, Neurology 45:325-31 (1995)). The present invention is not limited to a particular mechanism. Indeed, an understanding of the mechanism is not necessary to practice the present invention. Nonetheless, it is contemplated that ADHSP with the SPG-6 locus does not result from genetic imprinting.

A Mutation within the NIPA-1 Gene Causes ADHSP

In order to understand the molecular pathology surrounding ADHSP, four unique, non-imprinted and highly evolutionarily conserved genes were analyzed. These genes mapped proximal of the imprinted domain and within the pericentromeric region of chromosome 15q (Chai et al, Am J Hum Genet (2003 in press)). These candidate genes included "non-imprinted in Prader-Willi/Angleman locus 1 (NIPA-1) (SEQ ID NO: 1) (NCBI-BK001020) and NIPA2 (NCBI-BK001120) (Chai et al, Am J Hum Genet (2003 in press)), GCP5 (NCBI-AF272884) (Murphy et al, Mol. Biol. Cell 12:3340-3352 (2001)) and CYFIP1 (NCBI-NM_014608) (Koybayashi et al, J Biol Chem 273:291-295 (1998)); Schenk et al, Proc Natl Acad Sci (USA) 98:8844-8849 (2001)).

A nucleotide substitution at position 159 of the NIPA1 cDNA (159C>G; FIG. 1a) was identified which resulted in an amino acid substitution at position 45 of the NIPA-1 protein (T45R) in each affected subject (n=29) in ADHSP-ARK1 (FIG. 1b). In contrast, each unaffected subject (n=29) had only C at this position (FIG. 1b), which agrees with the known human genomic sequence (NCBI-NT_024668). 105 control subjects (ascertained through the Elderly Subjects Program of the University of Michigan Institute of Gerontology) were also examined. Each control subject had only C at position 159 of the NIPA1 cDNA.

Analysis of the coding sequence of the other three non-imprinted genes (GCP5, CYFIP1 and NIPA2) in two affected members of ADHSP-ARK1 and identified no disease-specific mutations.

The NIPA1 coding sequence in affected probands from 62 ADHSP kindreds, 6 probable autosomal recessive HSP kindreds, and 13 subjects with all signs and symptoms of but no family history ("apparently sporadic" spastic paraplegia) were analyzed. Affected subjects in one unrelated kindred (ADHSP-IRQ1; FIG. 1b) had precisely the same NIPA1 mutation (159C>G; FIG. 1b) as affected subjects in the ADHSP-ARK1 kindred. Unaffected subjects from ADHSP-IRQ1 kindred showed only the normal nucleotide (159C). Whereas the ADHSP-ARK1 kindred was linked to the SPG6 locus (Fink et al, Am J Hum Genet 56:188-92 (1995)), the ADHSP-IRQ1 kindred was too small for meaningful linkage analysis. Clinical features of the ADHSP-ARK1 affected individuals are typical of uncomplicated HSP of late-teenage to early-adult symptom onset (Fink et al, Neurology 45:325-31 (1995)). Clinical features of ADHSP-IRQ1 were similar: onset of insidiously progressive spastic weakness in both legs that began in late teen-age years and was associated with urinary urgency and mild vibratory sensation impairment in the toes.

Kindreds ADHSP-ARK1 and ADHSP-IRQ1 are of Irish and Iraqi ancestry, respectively. Analysis of haplotypes for polymorphic markers linked to this locus (D15S541, D15S542, D15S646, D15S817, D15S1021) showed no evidence of haplotype sharing between ADHSP-ARK1 and ADHSP-IRQ1 kindreds. This indicates that these two ADHSP families are not closely related and suggests that the same NIPA1 mutation arose independently in these ADHSP kindreds.

The present invention is not limited to a particular mechanism. Indeed, an understanding of the mechanism is not necessary to practice the present invention. Nonetheless, it is contemplated that ADHSP within the SPG-6 locus is caused by a mutation within the NIPA-1 gene.

ADHSP Operates Through a Mutation within the NIPA-1 Polypeptide

Disease-specific NIPA1 mutations in ADHSP-ARK1 and ADHSP-IRQ1 occur in NIPA1 exon 1 and change threonine to arginine at amino acid position 45 (T45R) (FIG. 2b). This amino acid is conserved in mouse, chicken and fish (zebrafish and Fugu) (Chai et al, Am J Hum Genet (2003 in press)). The present invention is not limited to a particular mechanism. Indeed, an understanding of the mechanism is not necessary to practice the present invention. Nonetheless, it is contemplated that the disease-specific NIPA1 mutation changing threonine to arginine at amino acid position 45 (T45R) occurs at the end of the first of nine transmembrane domains in the NIPA-1 polypeptide (FIG. 2b). NIPA-1 does not contain an AAA domain (as is present in spastin (Hazan et al, Nat Genet 23:296-303 (1999)) or GTPase domain (as is present in atlastin (Zhao et al, Nat Genet 29:326-331 (2001)) or bear other homology to genes that cause other forms of HSP. The present invention is not limited to a particular mechanism. Indeed, an understanding of the mechanism is not necessary to practice the present invention. Nonetheless, it is contemplated that NIPA-1 functions as a receptor or transporter. Many PWS or AS individuals have chromosome 15q class I deletions that include NIPA1 (FIG. 2a; (Chai et al, Am J Hum Genet (2003 in press)). The fact that such individuals do not exhibit progressive spastic paraplegia shows that NIPA1 haploinsufficiency does not cause progressive spastic paraplegia. The present invention is not limited to a particular mechanism. Indeed, an understanding of the mechanism is not necessary to practice the present invention. Nonetheless, it is contemplated that the NIPA1 T45R missense mutation identified in these ADHSP kindreds is pathogenic through a dominant negative, gain-of-function mechanism.

NIPA1 mRNA is expressed constitutively at low levels with 2.2- and 7.5-kb transcripts in all human tissues, but shows significant enrichment in the brain (FIG. 2c). The latter expression pattern is found throughout the central nervous system whereas spinal cord shows equal expression of the two NIPA1 mRNAs (FIG. 2c). The alternative mRNA isoforms arise from alternative polyadenylation within NIPA1 exon 5, and equivalent expression patterns are found for mouse (Chai et al, Am J Hum Genet (2003 in press)).

Discussion

Observations of the same NIPA-1 gene mutation (159 C>G; T45R) in two unrelated ADHSP kindreds that disrupts an inter-species conserved amino acid and which was absent in control subjects (N=105) shows the pathogenic significance of the NIPA T45R missense mutation. Discovery of NIPA1 mutations as the cause of SPG6-linked HSP shows an ability to diagnose HSP and to provide genetic counseling. The present invention is not limited to a particular mechanism. Indeed, an understanding of the mechanism is not necessary to practice the present invention. Nonetheless, it is contemplated that SPG6 arises from altered signal transduction and/or small molecule transport through a membrane. NIPA-1 and its ligand are an attractive target for therapeutic intervention in SPG6 and other spastic paraplegias. Identification of the NIPA-1 cellular and subcellular localization, function and ligand will aid an understanding of axonal neurodegeneration in HSP and will have important therapeutic implications.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for diagnosing the presence of hereditary spastic paraplegia in a human patient comprising: a) obtaining a sample from a human patient, and b) detecting the presence of a variation at position 159 of SEQ ID NO: 1, wherein the presence of a G at position 159 of SEQ ID NO: 1 is indicative of hereditary spastic paraplegia in the human patient.

2. The method of claim 1, wherein said sample is DNA.

3. The method of claim 1, wherein said sample is RNA.

4. A method of determining if an individual may be at risk for developing hereditary spastic paraplegia comprising
   a) analyzing a nucleic acid test sample obtained from the individual, wherein said test sample contains the NIPA-1 nucleic acid sequence;
   b) comparing the results of said analysis of the test sample of step a) with the results of the analysis of a control nucleic acid sample, wherein the control sample comprises a wild-type NIPA-1 nucleic acid, wherein said wild-type NIPA-1 nucleic acid comprises SEQ ID NO: 1; and
   c) determining the presence or absence of at least one mutation in said test sample NIPA-1 nucleic acid sequence, wherein the presence of a C to G change at position 159 of a NIPA-1 nucleic acid sequence of the test sample NIPA-1 nucleic acid sequence identifies said individual as being at risk for developing hereditary spastic paraplegia.

5. The method of claim 4, wherein the nucleic acid test sample is selected from the group consisting of DNA and RNA.

6. The method of claim 4, wherein the nucleic acid test sample is amplified prior to analysis.

7. The method of claim 4, wherein the mutation is in the coding region of the NIPA-1 gene.

8. The method of claim 4, wherein the analysis is selected from the group consisting of: sequence analysis; hybridization assays and computer based data analysis.

* * * * *

UNITED STATES PATENT AND TRADEMARK OFFICE
CERTIFICATE OF CORRECTION

| | | |
|---|---|---|
| PATENT NO. | : 7,332,282 B2 | Page 1 of 1 |
| APPLICATION NO. | : 10/921742 | |
| DATED | : February 19, 2008 | |
| INVENTOR(S) | : Fink et al. | |

It is certified that error appears in the above-identified patent and that said Letters Patent is hereby corrected as shown below:

In the Specification

Column 1, lines 8-11, should read as follows:

--This invention was made with government support under NS033645, NS038713 and ES010631 awarded by the National Institutes of Health. The Government has certain rights in the invention.--

Signed and Sealed this
Twenty-fifth Day of March, 2014

Michelle K. Lee
*Deputy Director of the United States Patent and Trademark Office*